(12) United States Patent
Brnjic et al.

(10) Patent No.: US 9,856,511 B2
(45) Date of Patent: Jan. 2, 2018

(54) PROTEASE DEUBIQUITINATING INHIBITOR SCREENING

(75) Inventors: Slavica Brnjic, Uppsala (SE); Padraig D'Arcy, Stockholm (SE); Rolf Larsson, Uppsala (SE); Stig Linder, Bromma (SE)

(73) Assignee: VIVOLUX AB, Uppsala (SE)

( * ) Notice: Subject to any disclaimer, the term of this patent is extended or adjusted under 35 U.S.C. 154(b) by 200 days.

(21) Appl. No.: 14/344,968

(22) PCT Filed: Sep. 6, 2012

(86) PCT No.: PCT/SE2012/000129
§ 371 (c)(1),
(2), (4) Date: May 7, 2014

(87) PCT Pub. No.: WO2013/039438
PCT Pub. Date: Mar. 21, 2013

(65) Prior Publication Data
US 2014/0370528 A1 Dec. 18, 2014

(30) Foreign Application Priority Data
Sep. 16, 2011 (SE) ...................................... 1100678

(51) Int. Cl.
*C12Q 1/37* (2006.01)
*C12Q 1/34* (2006.01)
*G01N 33/50* (2006.01)
*G01N 33/573* (2006.01)

(52) U.S. Cl.
CPC ................. *C12Q 1/37* (2013.01); *C12Q 1/34* (2013.01); *G01N 33/5011* (2013.01); *G01N 33/573* (2013.01); *G01N 2500/00* (2013.01); *G01N 2500/02* (2013.01)

(58) Field of Classification Search
CPC .......... C12C 1/37; C12C 1/34; G01N 33/573; G01N 2500/00; G01N 33/5748; G01N 2500/02; G01N 33/5011
See application file for complete search history.

(56) References Cited

U.S. PATENT DOCUMENTS

2007/0292907 A1 12/2007 Shi et al.
2010/0292129 A1 11/2010 Finley

FOREIGN PATENT DOCUMENTS

WO 2007/041568 A2 4/2007
WO 2008/147536 A1 12/2008
WO 2011/094545 A2 8/2011

OTHER PUBLICATIONS

Nishio et al. (Biochemical and Biophysical Research Communications 390 (2009) 855-860).*
Stone et al, J. Mol. Biol. 344:697-706 (2004).
Koulich et al, Mol. Biol. Cell, 19:1072-1082 (2008).
D'Arcy et al, Nature Medicine, 17(12):1636-1640 (online Nov. 6, 2011).
D'Arcy et al, Int. J. Biochem. Cell Biol., 44:1729-1738 (online Jul. 20, 2012).
Lee et al, Nature, 467:179-184 (Sep. 9, 2010).
Kapuria et al, Cancer Research, 70(22):9265-9276 (Nov. 15, 2010).
Wicks et al, Oncogene, 24:8080-8084 (2005).
Cutts et al, Int. J. Biochem. Cell Biol., 43:604-612 (online Dec. 25, 2010).

* cited by examiner

*Primary Examiner* — Tracy Vivlemore
*Assistant Examiner* — Carmencita M Belei
(74) *Attorney, Agent, or Firm* — Porter Wright Morris & Arthur LLP

(57) ABSTRACT

A method for screening a compound to determine whether the compound is a proteasome deubiquitinating inhibitor of high specificity comprises contacting the compound with human 19S regulatory particles (19S RP) of 26S proteasome and determining whether the compound inhibits activity of deubiquitinating (DUB) enzymes UCHL5 and USP14; inhibition of UCHL5 and USCP14 activities indicates that the compound is a proteasome deubiquitinating inhibitor of high specificity.

8 Claims, 16 Drawing Sheets

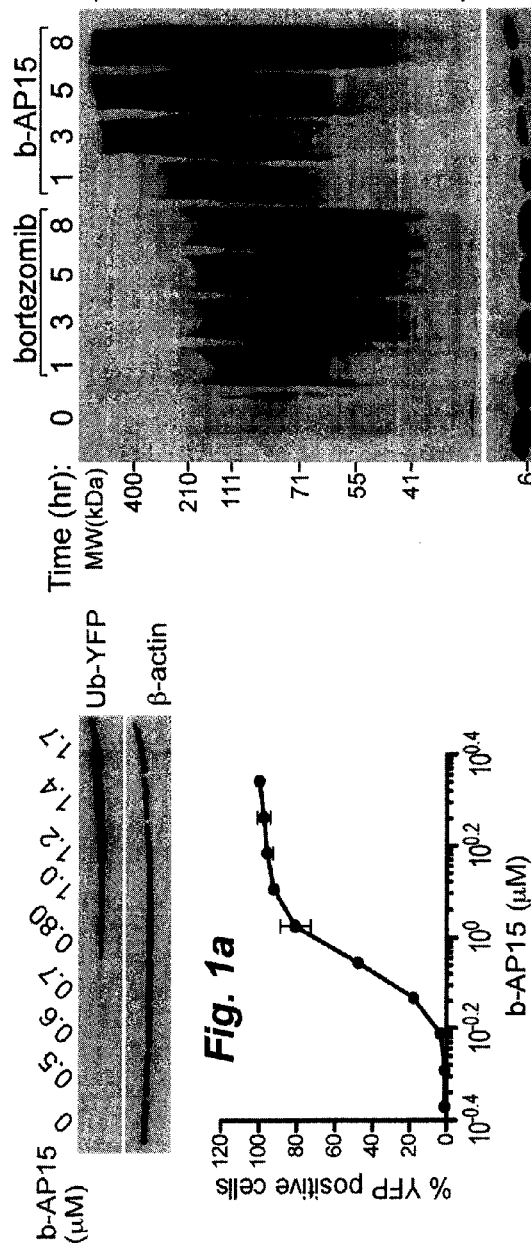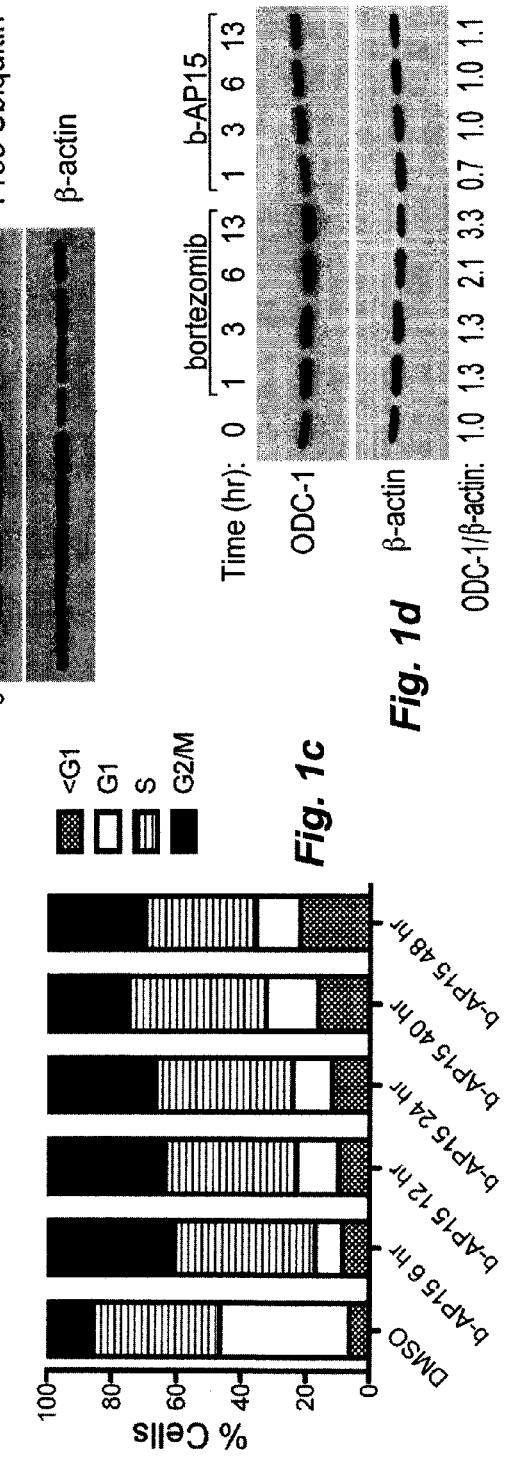

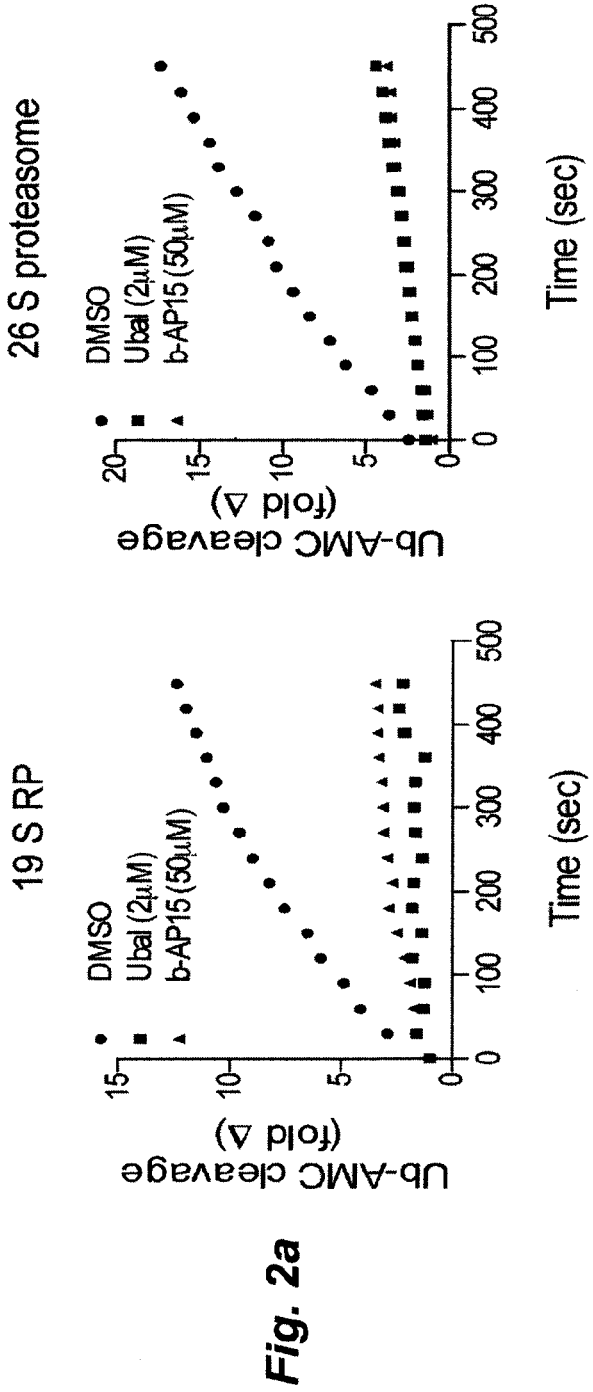
Fig. 2a
Fig. 2b
Fig. 2c

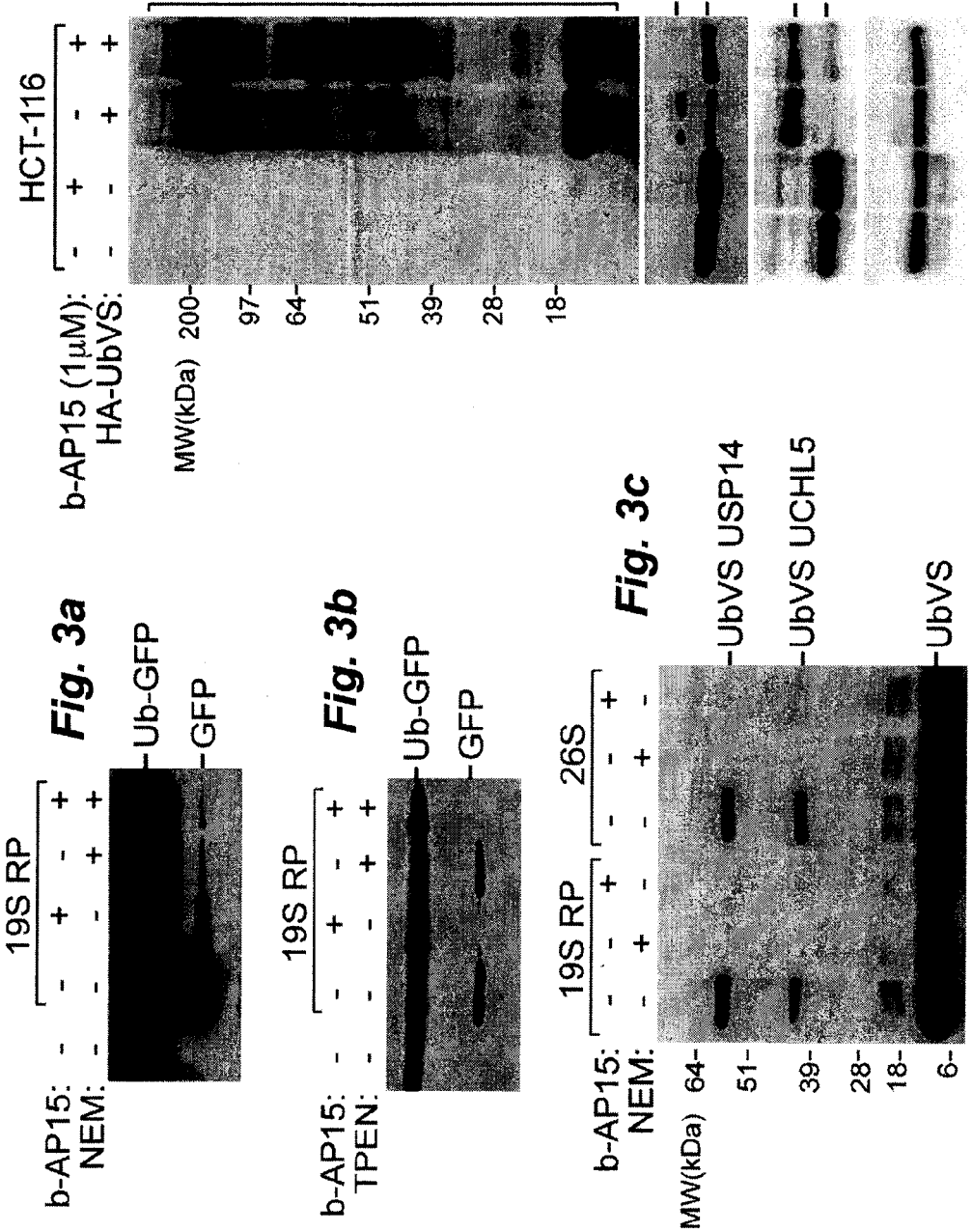

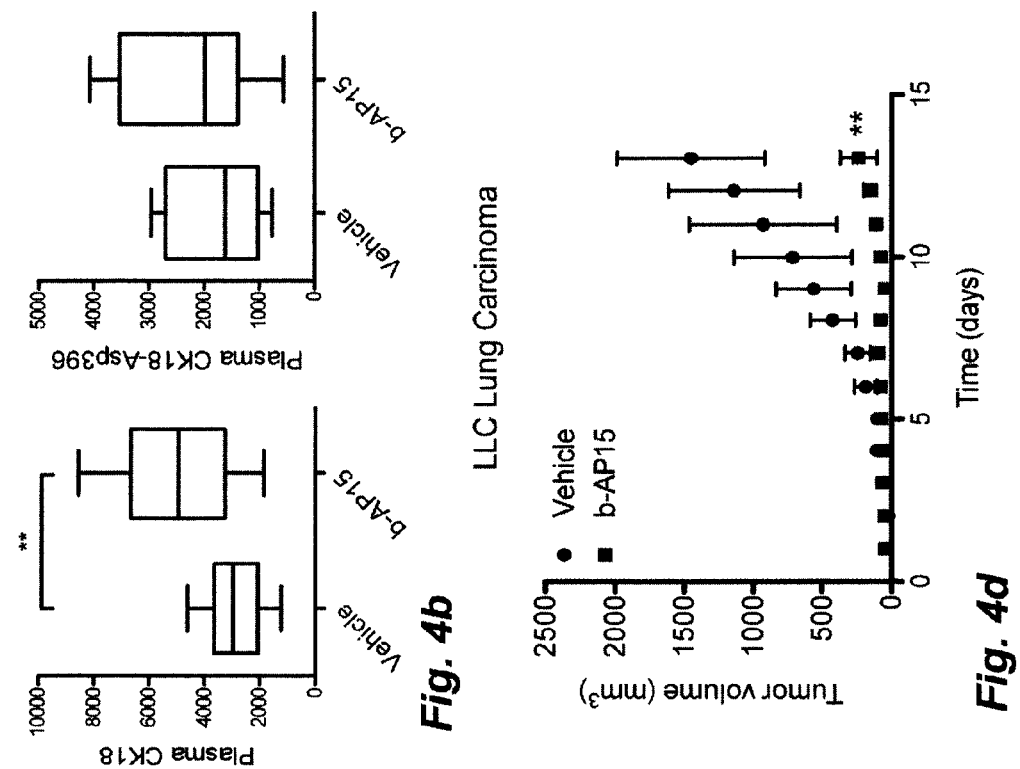
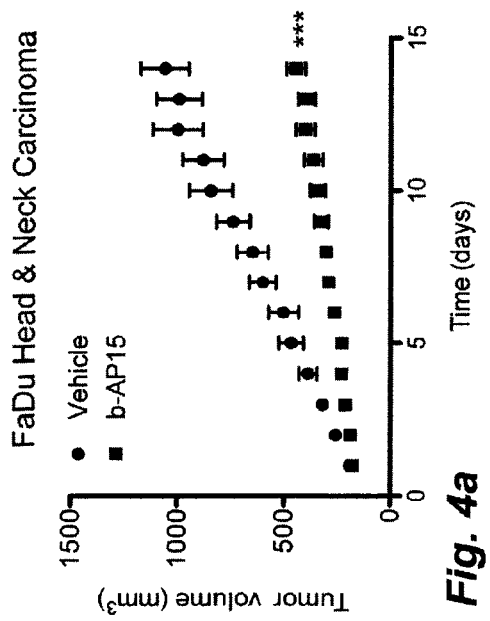
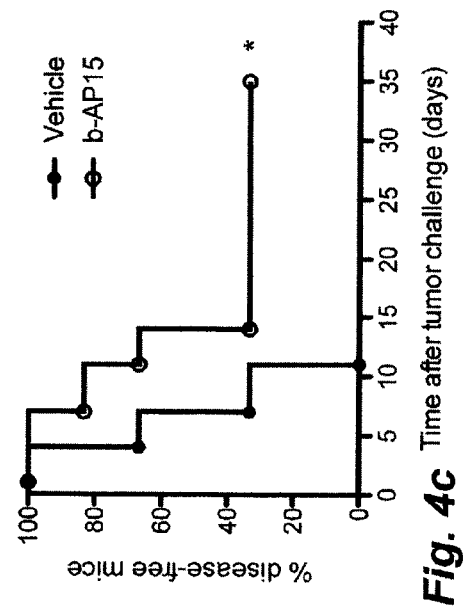
Fig. 4a  Fig. 4b  Fig. 4c  Fig. 4d

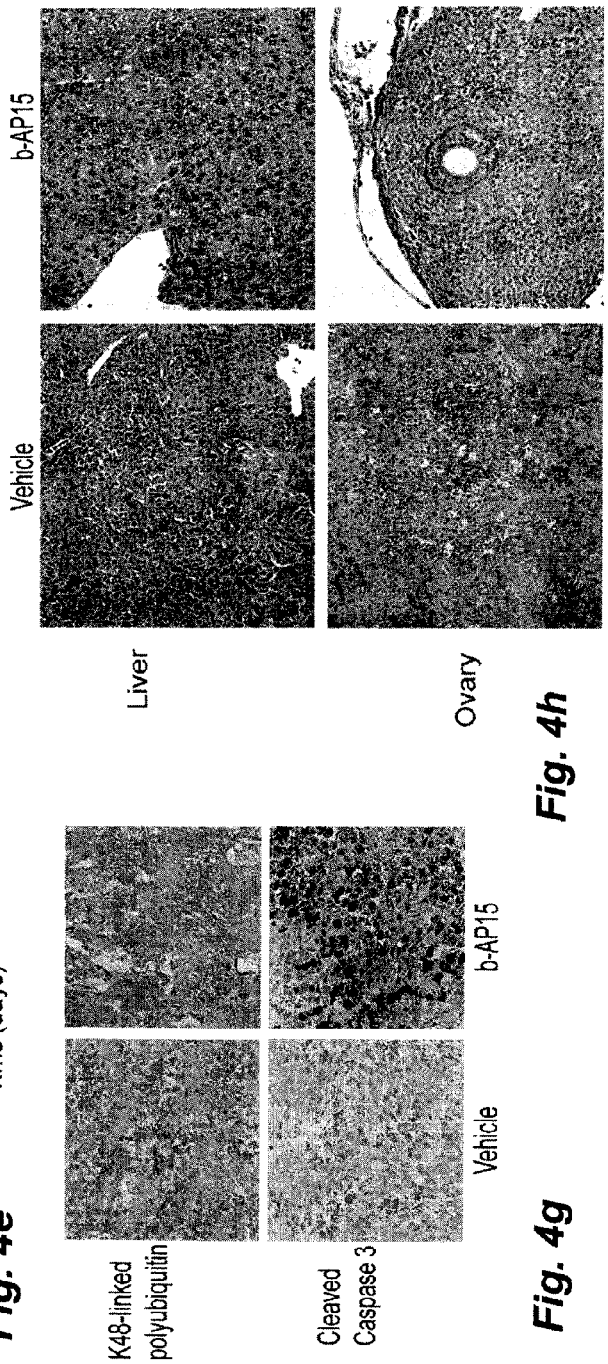
*Fig. 4h*
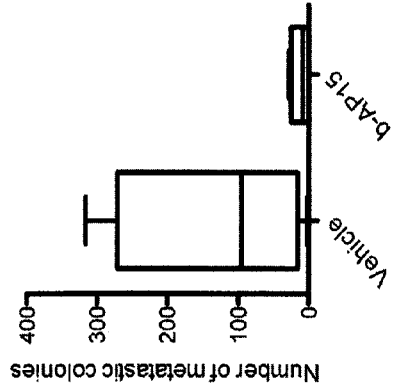
*Fig. 4f*
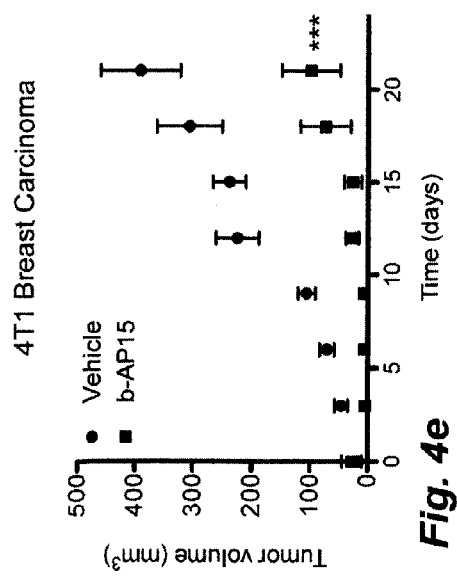
*Fig. 4e*
*Fig. 4g*

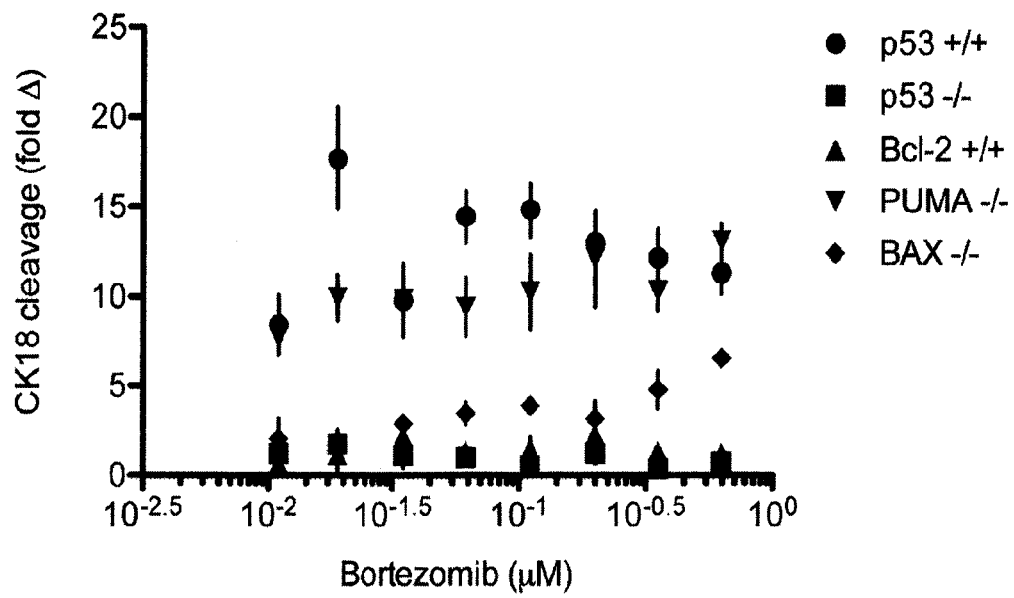
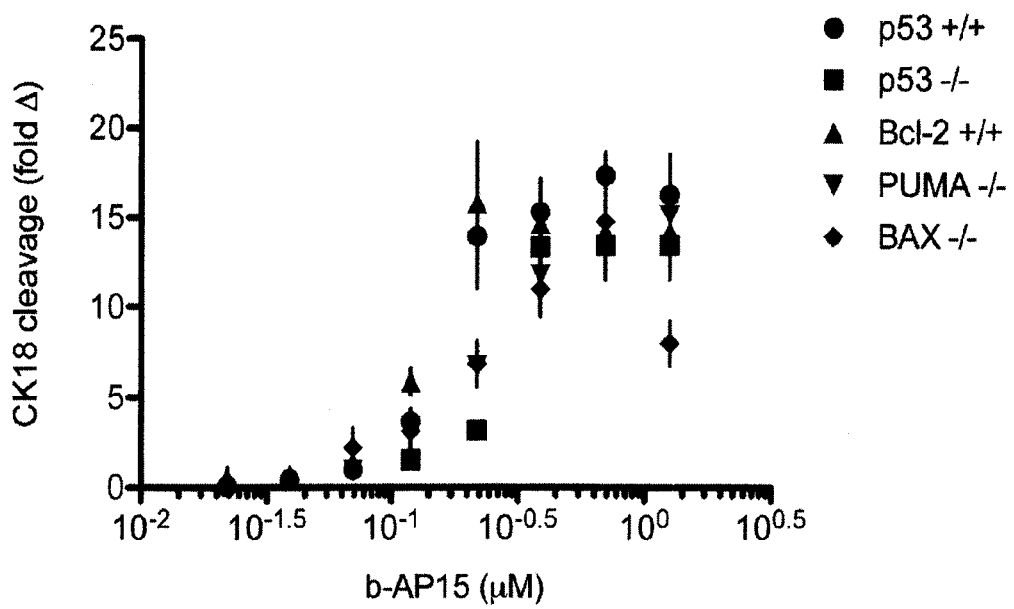
*Fig. 7*

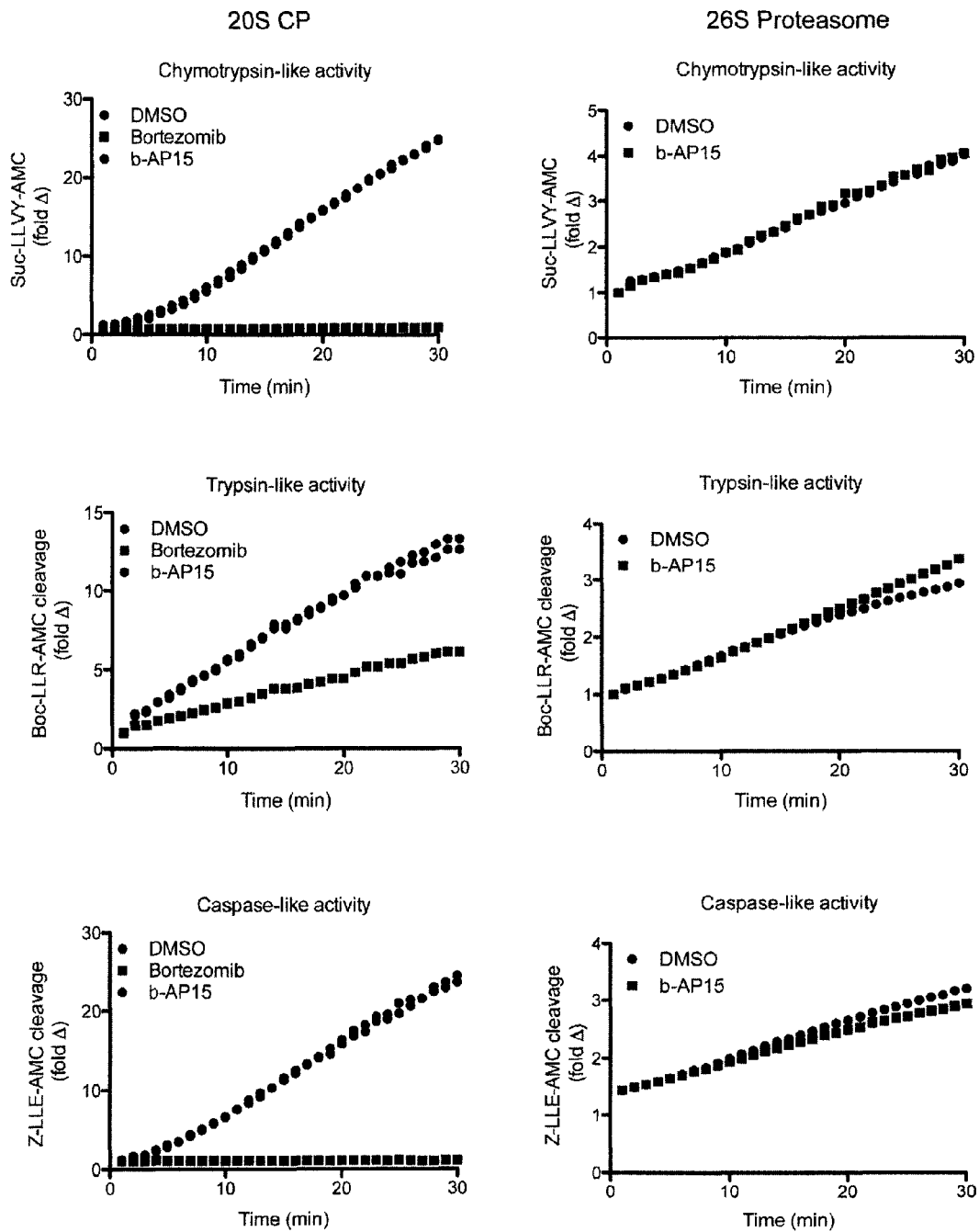
*Fig. 8a*      *Fig. 8b*

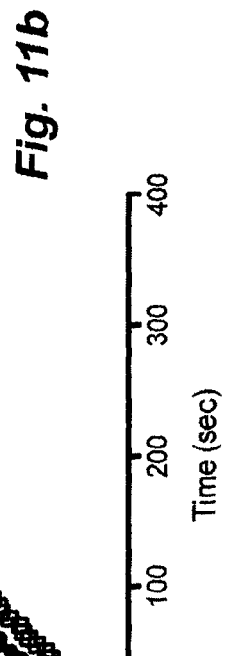
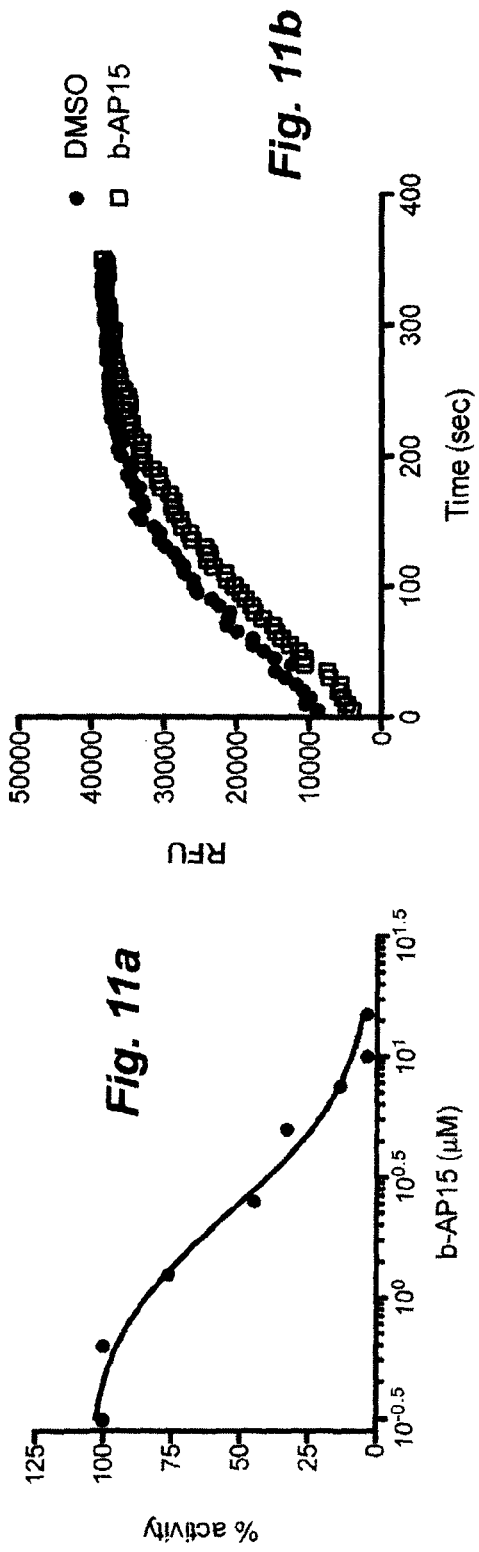
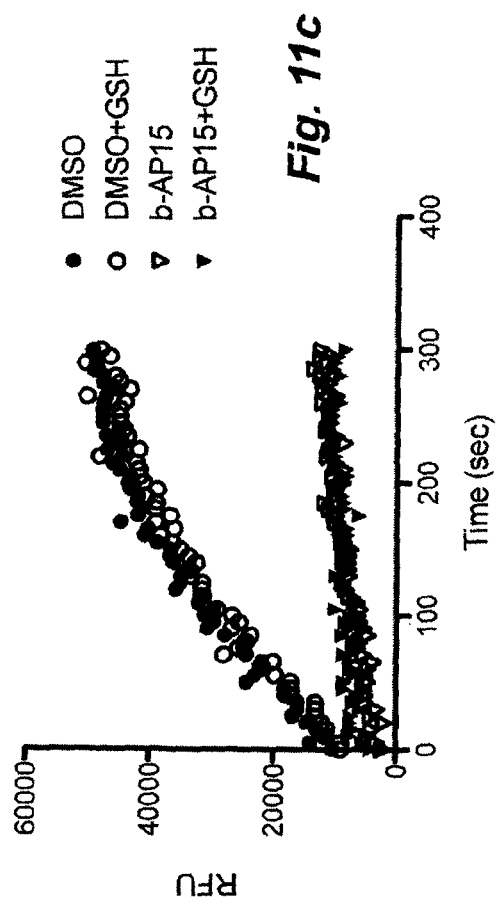
Fig. 11a
Fig. 11b
Fig. 11c

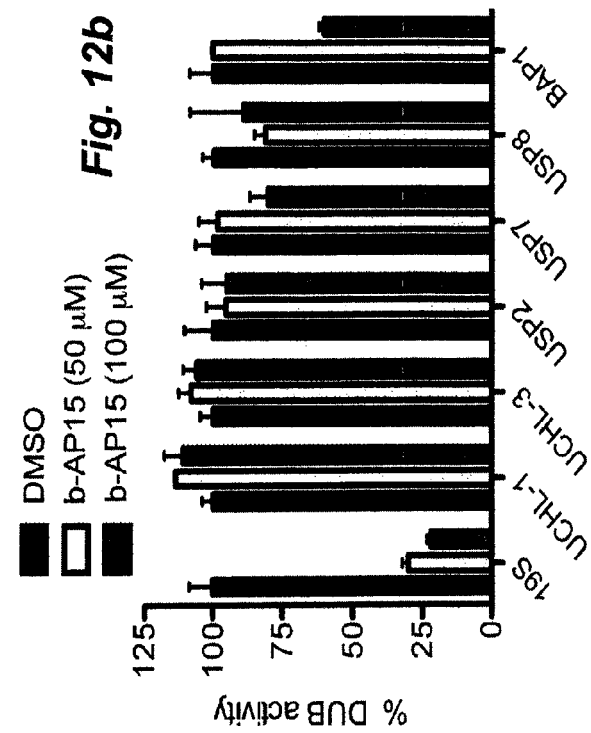
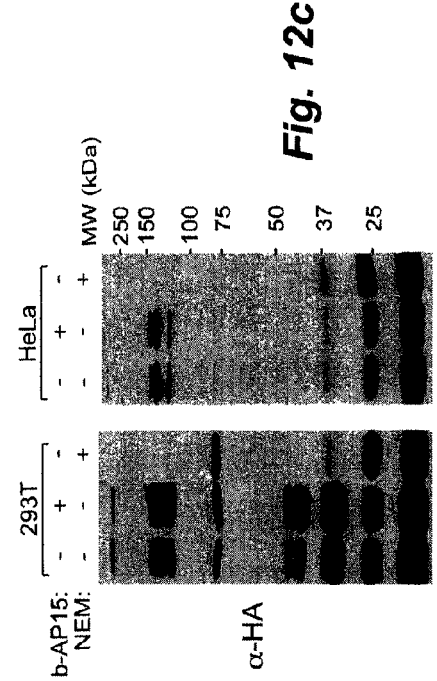
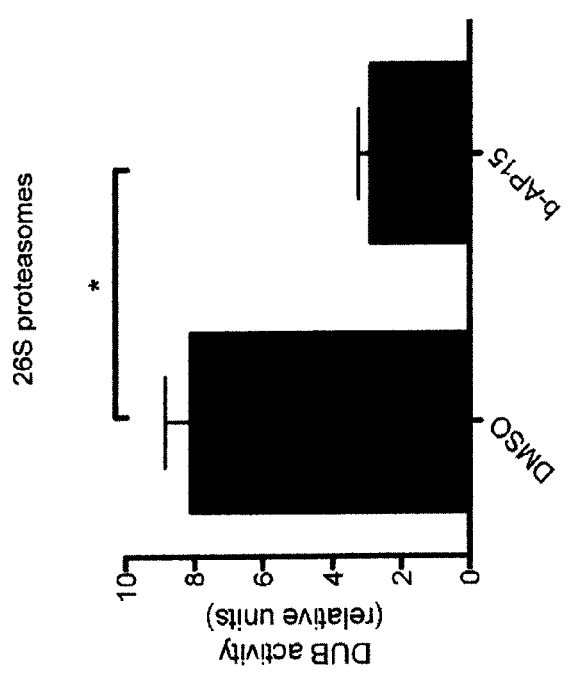
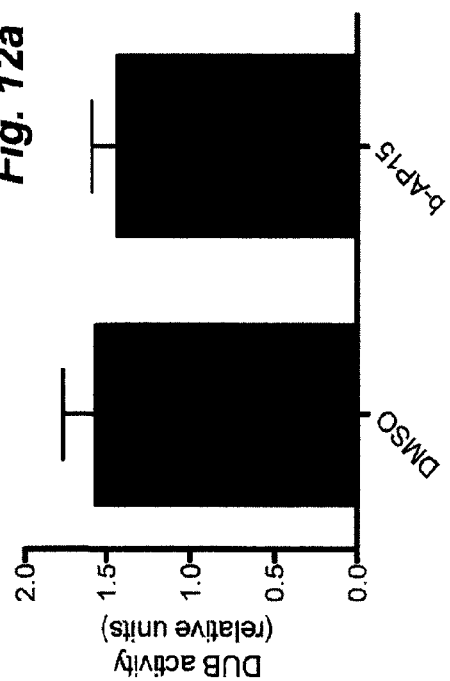
Fig. 12a
Fig. 12b
Fig. 12c

PROTEASE DEUBIQUITINATING INHIBITOR SCREENING

FIELD OF THE INVENTION

The invention relates to a method for screening a compound to determine whether the compound is a proteasome deubiquitinating inhibitor of high specificity.

BACKGROUND OF THE INVENTION

Tumor cells display enhanced sensitivity to disruptions in the ubiquitin-proteasome system (UPS) making this an attractive target for the development of anti-cancer therapies (1). Ubiquitin-tagged substrates are recognized for destruction by the 26S proteasome; a multi-subunit complex comprising a proteolytic 20S core (20S CP) capped by 19S regulatory particles (19S RP) (2,3). The 20S CP has evolved as an important target for anti-cancer drug development, resulting in the approval of bortezomib (Velcade®) for treatment of myeloic leukemia (4). The low molecular weight compound b-AP15 (NSC687852) is known to induce p53-independent and cathepsin-D-dependent apoptosis (5,6).

OBJECTS OF THE INVENTION

It is an object of the invention to provide a method for screening a compound to determine whether the compound is a proteasome deubiquitinating inhibitor of high specificity.

Another object of the invention is to provide proteasome deubiquitinating inhibitors of high specificity identified by the method.

Further objects of the invention will become evident by studying the following summary of the invention, a number of preferred embodiments thereof illustrated in a drawing, and the appended claims.

SUMMARY OF THE INVENTION

According to the present invention the known compound b-AP15 is recognized as pertaining to a novel class of proteasome inhibitors that abrogate the deubiquitinating (DUB) activity of the 19S RP.

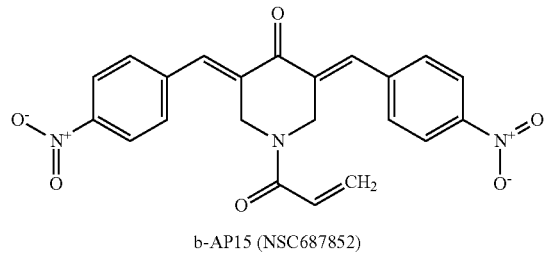 [SMILES: C=CC(=O)N1C/C(=C\c2ccc([N+](=O)[O-])cc2)C(=O)/C(=C/c2ccc([N+](=O)[O-])cc2)C1]

b-AP15 (NSC687852)

According to the invention it has been found that b-AP15 inhibits the activity of two 19S RP DUBs, UCHL5 and USP14 but does not affect non-proteasomal DUBs. Consistent with DUB inhibition, treatment with b-AP15 causes the accumulation of polyubiquitinated proteins of higher molecular weight in comparison with bortezomib treatment, and results in a stronger unfolded protein response. According to the invention, it has also been found that apoptosis induction by b-AP15 differs from that of bortezomib by being insensitive to disruption of the p53 tumor suppressor and insensitive to overexpression of the apoptosis inhibitor Bcl-2. It has furthermore been found that treatment with b-AP15 does inhibit growth of solid tumor xenografts. In consequence, inhibiting the DUB activity of the 19S RP is a viable option for the treatment of cancer. For this reason, compounds sharing the activity pattern of b-AP15 are candidates for the development of potent anti-cancer drugs. The method by which b-AP15 has been identified to possess the aforementioned valuable properties thus is applicable to other compounds of unknown activity pattern and useful for identifying whether they share or not the aforementioned properties of b-AP15. If shared, compounds so identified have potential as candidates for the development of anti-cancer medicines.

Specifically, according to the present invention is disclosed a method for screening a compound to determine whether the compound is a proteasome deubiquitinating inhibitor of high specificity, the method comprising contacting the compound with human 19S regulatory particles (19S RP) of 26S proteasome and determining whether the compound inhibits activity of deubiquitinating (DUB) enzymes UCHL5 and USP14, wherein inhibition of UCHL5 and USP14 activities indicates that the compound is a proteasome deubiquitinating inhibitor of high specificity.

According to a preferred aspect of the invention, the method comprises the additional step of determining whether the compound affects activity of non-proteasomal associated DUB enzymes. It is preferred for the non-proteasomal associated DUB enzymes to comprise at least one of UCHL1, UCHL3, USP2, USP7, USP8.

According to another preferred aspect of the invention, the determination of the inhibition of UCHL5 and USP14 activities is conducted with an assay performed with human 19S RP with ubiquitin-AMC or HA-ubiquitin vinyl sulfone as substrate.

To further characterize the effects elicited by b-AP15 the gene expression signature of cells treated with this compound was compared with a collection of expression signatures for over 1300 bioactive compounds provided by the CMAP database (www.broad.mit.edu/cmap) (7). Treatment with b-AP15 induced a gene expression profile comparable to that of several characterized proteasome inhibitors, MG-262 (8), 15.prostaglandin J2 (9), celastrol (10) and withaferin A (11) being amongst the most active inhibitors. To confirm that b-AP15 blocks cellular proteasome function, a reporter cell line was used, which expresses ubiquitin tagged to yellow fluorescent protein (UbG76V-YFP) that is constitutively targeted for proteasomal degradation (12). Immunoblotting and flow cytometry revealed a dose dependent accumulation of the Ub-YFP reporter (IC50=0.8 µM) suggesting an impairment of proteasome function. Since inhibition of proteasome function is characterized by defects in ubiquitin turnover (13) colon carcinoma HCT116 cells were treated with the compound and the level of ubiquitin conjugation analyzed by immunoblotting. Treatment with b-AP15 caused the time dependent accumulation of polyubiquitinated proteins of a higher molecular weight in comparison with the 20S CP inhibitor bortezomib, suggesting that b-AP15 inhibits an alternative branch of the UPS.

The turnover of many cell cycle regulatory proteins is controlled by the UPS including inhibitors of the cyclin-dependent kinases p21 Cip1, p27 Kip1 and the tumor suppressor p53 (4). Treatment with b-AP15 increased their levels in a dose dependent manner. In contrast no increase was observed in respect of the level of DNA damage markers such as phosphorylated p53 (at Ser 15) (14) or H2AX (at Ser 139) (15), suggesting that b-AP15 is not a genotoxic agent. The accumulation of cell cycle regulators was concomitant with cell cycle arrest in the G2/M phase boundary. As early as 6 h post b-AP15 treatment cells began to accumulate at the G2/M phase; exposure for a longer time resulted in an increase in sub G1 DNA content.

The increase in sub G1 DNA content is associated with (i) activation of the apoptosis mediator caspase-3 and (ii) with cleavage of the caspase substrates poly-ADP ribose polymerase (PARP) and cytokeratin-18. Caspase cleavage of cytokeratin-18 and decreased cell viability were observed at the same concentrations range that induced accumulation of the Ub-YFP reporter. Apoptosis induction by bortezomib is dependent on p53 and inhibited by overexpression of the Bcl-2 protein (16,17). By use of isogenic clones of HCT116 colon cancer cells it was found that b-AP15 induces caspase cleavage of cytokeratin-18 not affected by genetic disruption of p53 or overexpression of Bcl-2. Furthermore, genetic disruption of the apoptotic regulators BAX or PUMA does not affect b-AP15 sensitivity, whereas bortezomib-induced apoptosis is inhibited.

20S CP contains the $\beta1$, $\beta2$ and $\beta4$ proteolytic subunits responsible for caspase-like, trypsin-like and chymotrypsin-like activities of the proteasome, respectively (18). In vitro experiments using activity-specific substrates do not show alteration in any of these activities following treatment with molar excess of b-AP15. Further substrate overlay assays revealed the presence of doubly and singly capped 26S proteasomes following treatment with b-AP15 suggesting that the decrease in proteasomal function observed in cells is not caused by disassociation of the 19S RP and 20S CP 19,20.

b-AP15 comprises an $\alpha$-$\beta$ dienone entity with two sterically accessible $\beta$ carbons. A structurally similar pharmacophore has been earlier described to be comprised by a class of ubiquitin isopeptidase inhibitors (21). However, when cellular DUB activity was tested using ubiquitin 7-amido-4-methylcoumarin (Ub-AMC) on b-AP15 treated cells, no reduction in Ub-AMC cleavage could be observed. This demonstrates that b-AP15 is not a general DUB inhibitor. In the opinion of the present inventors the similarities in pharmacophore structure and the data showing that b-AP15 inhibits proteasome activity independent of the 20S CP indicate that b-AP15 represents a novel class of proteasome inhibitors that block the deubiquitinating activity of the 19S RP.

In vitro assays using Ub-AMC and purified 19S RP or 26S proteasomes confirmed that b-AP15 inhibits the deubiquitinating activity of both the 19S RP and 26S proteasome. To this end the ability of b-AP15 to inhibit cleavage of recombinant ubiquitin-GFP was assessed. Recombinant ubiquitin-GFP is a substrate for 19S RP DUB activity (22). Treatment of 19S RP with b-AP15 effectively inhibited the cleavage of Ub-GFP. The type of ubiquitin bonds present in the polyubiquitin chain determines the fate of an ubiquitin-modified substrate. K48 linked polyubiquitin chains generally targets conjoined proteins for degradation (23), whereas K63 linked chains are involved in non-proteolytic roles including DNA repair (24) and mitotic chromosome segregation (25). Ubiquitin chain disassembly reactions revealed that b-AP15 inhibited 19S RP processing of both K48 and K63 linked ubiquitin tetramers. The inhibition of ubiquitin chain disassembly observed could account for the accumulation of high molecular weight ubiquitin conjugates in b-AP15 treated cells.

The deubiquitinating activity of the proteasome is attributed to the action of three DUBs, UCHL5, USP14 and POH1, all localized within the 19S RP 26-28. Both UCHL5 and USP14 are sensitive to N-ethylmaleimide (NEM), a general inhibitor of cysteine proteases, whereas POH1 is insensitive to inhibition by NEM but sensitive to metal chelators such as N,N,N,N-tetrakis-(2-pyridylmethyl)ethylenediamine (TPEN) (29). Inhibition experiments showed that residual DUB activity was present even after co-treatment of 19S RP with NEM and b-AP15. This residual DUB activity was abolished upon co-treatment of 19S RP with b-AP15 and TPEN, suggesting that b-AP15 primarily inhibits one or both of the NEM sensitive DUBs. To identify specifically which DUBs were inhibited by b-AP15 treatment, competitive labelling experiments were performed using hemagglutinin tagged ubiquitin vinylsulphonone (HA-UbVS), an active site directed probe that irreversibly reacts with DUBs of the cysteine class (26). Incubation of 19S RP or 26S proteasomes with b-AP15 abolished Ub-VS labelling of two DUBs of molecular weights corresponding to UCHL5 and USP14 without affecting the activity of two related non-proteasomal associated DUB enzymes, UCHL1 and USP5.

To confirm that the results obtained by in vitro assays can be extended to cytotoxic effects observed on cells, additional labelling experiments were performed, using HA-UbVS on lysates derived from drug-treated cells (1 µM, 3 h). Immunoblot analysis showed a downward shift in the molecular weight of both USP14 and UCHL5 due to a loss of activity and decreased HA-UbVS labelling. Importantly, no alteration in the overall HA-UbVS labelling profile of DUBs from treated cells or treated cell lysates was observed, which is an additional confirmation of b-AP15 not being a general DUB inhibitor.

In order to investigate the effect of b-AP15 on tumor growth in vivo, the compound was administered to mice bearing either a human tumor or mouse xenografts. FaDu head and neck carcinoma were chosen as a SCID mouse xenograft both as a model for a p53mut tumor and since this model is suitable for studies using circulating cell death biomarkers (30). Significant inhibition of FaDu tumor growth was observed following daily treatment with b-AP15 (treated/control tumor volume, T/C=0.4, p=<0.001). Similarly b-AP15 (day on/2 day off schedule) inhibited tumor growth in C57BL/6J mice bearing lung carcinomas (T/C=0.16, p=<0.01). No adverse side effects were observed in the b-AP15 treated group with an average weight loss of <5% at the conclusion of the study. To examine whether b-AP15 promotes tumor cell death in vivo, plasma levels of cytokeratin-18 (CK18) were analyzed. Cytokeratin-18 is a biomarker for apoptosis and cell death (30,31); assays specific to this human protein were used. b-AP15 treatment results in significant increase in levels of human CK18 derived from FaDu tumors in the circulation (p=0.01). Levels of caspase cleaved CK18 (CK18-Asp396) increased moderately compared with total levels, suggesting that apoptosis is not the exclusive mechanism of cell death in b-AP15 treated tumors. To investigate the ability of b-AP15 to inhibit proteasome deubiquitination in vivo, accumulation of poly-ubiquitin conjugates was analyzed by means of antibodies specific for K48 linked polyubiquitin chains. Histological analysis of treated tumors confirmed the accumulation of poly-ubiquitin conjugates. These results indicate that b-AP15 inhibits proteasome DUB activity and tumor growth in vivo.

Ubiquitin C-terminal hydrolases (UCH) and ubiquitin specific proteases (USP) are major subgroups of the approximately one hundred DUBs encoded by the human genome (32). The mechanism of specificity of b-AP15 for UCHL5 and USP14 in the 19S RP may be related to unique conformations of these enzymes in the 19S RP or due to drug-induced alterations of the 19S RP structure. The present findings are consistent with reports in the art indicating that loss of both UCHL5 and USP14, unlike loss of either one alone, leads to the accumulation of polyubiquitinated proteins and inhibition of cellular protein degradation (33).

The ability of b-AP15 to induce apoptosis of cells overexpressing Bcl-2 or defective in p53 is of particular interest in consideration of the role of these proteins in bortezomib resistance (16,17,34). Both b-AP15 and bortezomib are blocking cellular proteasome activity but induce apoptosis by different pathways. While not wishing to be bound by theory, the observation that DUB inhibition is associated with high molecular weight ubiquitin-substrate complexes seems to be of particular relevance in this context. Strong expression of chaperone genes was observed in bAP15-treated cells, indicating induction of a proteotoxic response.

In the following the invention will be described in greater detail by reference to preferred embodiments thereof illustrated by a drawing comprising a number of figures.

DESCRIPTION OF THE FIGURES

The figures of the drawing illustrate:
FIGS. 1a-1f Inhibition by b-AP15 of the ubiquitin-proteasome system;
FIGS. 2a-2e Inhibition b-AP15 of deubiquitination by the 19S RP;
FIGS. 3a-3d Inhibition by b-AP15 of the 19S RP DUBs UCHL5 and USP14;
FIGS. 4a-4h Inhibition by b-AP15 of tumor growth in vivo;
FIG. 7 Dose response curves of apoptosis induction in isogenic clones of HCT-116 cells;
FIGS. 8a, 8b Absence of inhibition b-AP15 of proteasome proteolytic activity;
FIGS. 11a-11c Biochemical characterization of b-AP15 binding;
FIGS. 12a-12c b-AP15 not being a general DUB inhibitor.

DESCRIPTION OF PREFERRED EMBODIMENTS

Methods

Figure 1E:
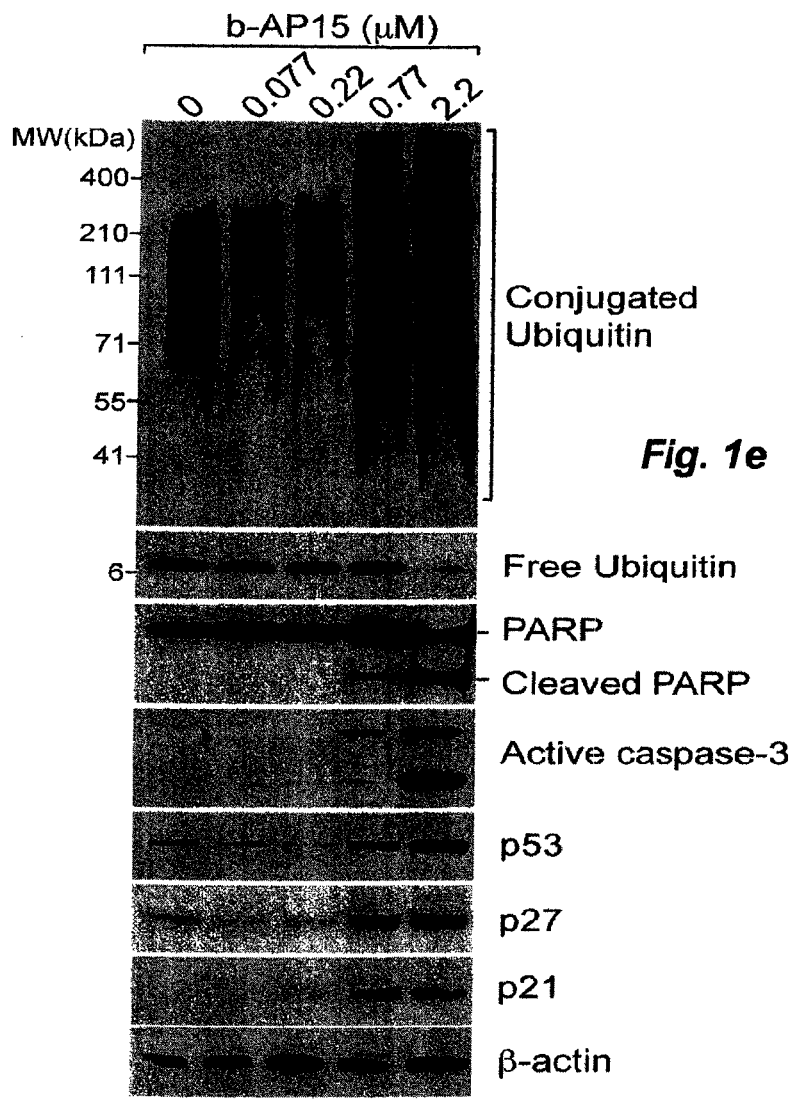

In vitro proteasome activity assays were performed in black 96-well microtiter plates using human 20S proteasome (Boston Biochem) in reaction buffer (25 mM Hepes, 0.5 mM EDTA, 0.03% SDS) with Suc-LLVY-AMC, Z-LLE-AMC or Boc-LRRAMC used as substrates for proteasome activity. De-ubiquitinase activity assays were performed with human 19S RP (Boston Biochem) with ubiquitin-AMC as substrate. For xenograft studies a 100-µl-cell suspension containing $1 \times 10^6$ FaDu head-neck or $2 \times 10^5$ Lewis Lung Carcinoma (LLC) cells were injected subcutaneously into the flank of SCID or C57BL/6J mice. Upon tumor take mice were randomized into control or treatment groups and administered with 5 mg kg$^{-1}$ b-AP15 or vehicle. In vivo levels of apoptosis and cell death were determined from the detection of caspase cleaved and total levels of cytokeratin-18 in plasma using M30 Apoptosense® and M65 ELISA®s assays (Peviva). The methods are described below in detail.

Reagents.

Reagents were obtained from the following sources: 20S proteasome (E-360), 26S proteasome (E-365), 19S proteasome (E-366), Suc-LLVY-AMC (S-280), Z-LLE-AMC (S-230), Boc-LRR-AMC (S-300), Ubiquitin-AMC (U-550), Tetra-ubiquitin K63 (UC-310), Tetra-ubiquitin K48 (UC-210), deconjugating enzyme set (KE10), HA-Ubiquitin Vinyl Sulfone (U-212) (Boston Biochem); anti-β actin (AC-15), ODC-1 (HPA001536) (Sigma Aldrich); anti-LC-3 (2775), anti-GAPDH (2118), anti-p44/42 MAPK (4695), anti-Phospho-p44/42 MAPK (9101) (Cell Signaling); N-ethylmaleimide (34115) (EMD Chemicals); anti-Ubiquitin K48 (Apu2), anti-Ubiquitin (MAB1510) (Millipore); anti-p53 (DO1), anti-UCHL5 (H-110), Hdm2 (SMP14) (Santa Cruz); anti-PARP (C2-10), anti-p27 (G173-524), anti-active Caspase 3 (C92-605) (BD Biosciences); anti-USP14 (A300-919A) (Bethyl Laboratories); anti-HA (12CA5) (Roche); b-AP15 (NSC687852) was obtained from the Developmental Therapeutics Program of the US National Cancer Institute (http://www.dtp.nci.nih.gov) or synthesized by Onco-Targeting AB (Uppsala, Sweden). Bortezomib was obtained from the Department of Oncology, Karolinska Hospital, Sweden.

Cell Culture.

MCF7 cells were maintained in MEM/10% fetal calf serum. HCT-116 p53+/+, p53−/−, Bcl-2+/+, PUMA−/− and BAX−/− cells were maintained in McCoy's 5A modified medium/10% fetal calf serum. The HCT-116 p53+/+, p53−/−, PUMA−/− and BAX−/− were generated as described (36). The HCT-116 Bcl-2+/+ cell line was generated by transfecting parental HCT-116 p53+/+ cells with pCEP4 Bcl-2 (Addgene plasmid 16461) (37) and isolating high expression clones. FaDu and LLC3 cells were maintained in DMEM high glucose medium supplemented with 10% fetal calf serum, Na pyruvate, Hepes and non-essential amino acids. 4T1.12B carcinoma cells were maintained in RPMI medium supplemented with 10% fetal calf serum. The proteasome reporter cell line MelJuSo Ub-YFP was generated as described (38). Cells were maintained in Dulbecco's Modified Eagle's Medium/10% fetal calf serum. The retinal epithelial cell line was generated as described (39). All cells were maintained at 37° C. in 5% $CO_2$.

Connectivity Map Analysis.

The microarray based gene expression analysis and the Connectivity Map (CMAP) analysis was performed as previously described (40). Briefly, MCF7 cells were exposed to b-AP15 (1 µM, 6 h) or vehicle (0.1% DMSO, 6 h). RNA was isolated (RNeasy miniprep kit, Qiagen) followed by quality control, labelling and hybridization to Genome U133 Plus 2.0 arrays (Affymetrix Inc). Raw data was normalized using Mas5 (Affymetrix Inc.) and rank ordered. For selection of the 30 most induced (up tags) and the 30 most suppressed (down tags) transcripts the following criteria were used: Up tags, present call and expression over 300 arbitrary in the b-AP15 experiment; Down tags, present call after both b-AP15 and vehicle treatment, and expression over 300 arbitrary units in the vehicle experiment. For CMAP compatibility only tags (i.e. probes) present on HG U133A were used. Raw and normalized expression data have been deposited at Gene Expression Omnibus (http://www.ncbi.nlm.nih.gov/geo/) with accession number GSE24150.

Proteasome and DUB Inhibition Assays.

In vitro proteasome activity assays using 20S CP (2 nM) (Boston Biochem) were performed at 37° C. in 100-µl reaction buffer (25 mM Hepes, 0.5 mM EDTA, 0.03% SDS). Samples were incubated for 10 min with indicated compound followed by addition of 10 µM Suc-LLVY-AMC, Z-LLE-AMC or Boc-LRR-AMC for the detection of chymotrypsin-like, caspase-like and trypsin-like activity respectively. For DUB inhibition assays 19S RP (5 nM), 26S (5 nM) UCH-L1 (5 nM), UCH-L3 (0.3 nM), USP2CD (5 nM) USP7CD (5 nM) USP8CD (5 nM) and BAP1 (5 nM) were incubated with b-AP15 followed by addition of ubiquitin-AMC (1000 nM). Fluorescence was monitored using Wallac Multilabel counter or Tecan Infinite M1000 equipped with 360 nm excitation and 460 nm emission filters. Substrate overlay assays. Native gel electrophoresis was performed as described (41). In brief 4 µg of purified 26S proteasome (Boston Biochem) was mixed with 10 or 50 µM b-AP15 and incubated at 37° C. for 10 min. Samples were resolved on 4% non-denaturing PAGE. Gels were submerged in assay buffer (20 mM Tris-HCL, 5 mM $MgCl_2$, 1 mM ATP, 0.1 mM Suc-LLVY-AMC) and proteasomes were visualized under UV illumination.

Ubiquitin-Cleavage Assay.

The recombinant Ub-GFP plasmid pet19b Ub-M-GFP was generated as described (42). In brief recombinant Ub-GFP was purified from BL21 E. coli cells by His affinity purification. For cleavage assays 19S RP (25 nM) was incubated with 10 mM NEM, 250 µM TPEN or 50 µM b-AP15 for 10 min followed by the addition of recombinant Ub-GFP (200 nM). Ubiquitin chain disassembly reactions were performed essentially as above except K48- or K63-linked ubiquitin tetramers (50 ng) were substituted for Ub-GFP. The level of Ub-GFP cleavage or ubiquitin disassembly was determined by immunoblotting with anti ubiquitin antibodies. The ubiquitinated Hdm2 substrate was generated according to the Boston Biochem protocol (K-200). For the cleavage assay 19S RP (25 nM) was incubated with 50 µM b-AP15 or DMSO for 10 min followed by the addition of ubiquitinated Hdm2 substrate (100 nM). The cleavage of ubiquitinated Hdm2 substrate and ubiquitinated Hdm2 was determined by immunoblotting with anti-Hdm2 antibodies.

Proteasome Isolation:

HCT-116 cells were treated with bortezomib (100 nM) or b-AP15 (1 µM) for 3 hours. After stimulation, the cells were lysed in 50 mM HEPES pH 7.4, 250 mM sucrose, 10 mM $MgCl_2$, 2 mM ATP, 1 mM DTT and 0.025% digitonin. Samples were sonicated briefly and incubated for 15 min on ice. Proteasomes from these samples were isolated according to the manufacturer's protocol.

UbVS Labelling of DUBs.

For labelling of DUBs in cell lysates sub confluent cells were harvested by trypsinization, washed three times with PBS, and centrifuged at 1500 RPM for 5 min. Cell pellets were lysed with buffer (50 mM HEPES pH 7.4, 250 mM sucrose, 10 mM $MgCl_2$, 2 mM ATP, 1 mM DTT) on ice for 15 min. Debris was removed by centrifugation and 25 µg of protein was labelled with 1 µM HA-UbVS for 30 min at 37° C. Samples were resolved by SDS-PAGE and analyzed by immunoblotting with indicated antibodies.

Determination of Cell Apoptosis and Viability.

For determination of apoptosis parental HCT-116 p53+/+ cells were treated with the increasing doses of bortezomib or b-AP15 for 24 h. Treatment doses were based on the drug concentration that resulted in maximal apoptosis over a 24 h period. HCT-116 cells were seeded in 96-well microtiter plates at 10,000 cells per well and incubated overnight. Cells were treated with indicated drug for 24 h. At the end of the incubation period, NP40 was added to the tissue culture medium to 0.1% and 25 µl of the content of each well was assayed using the M30-Apoptosense® ELISA as previously described (43). Cell viability was determined by measuring acid phosphatase activity or using the FMCA method (44). For the acid phosphatase activity cells were seeded at 5000 cells per well in 96-well culture plates and incubated for 12 h at 37° C. Compounds were added to the cells in growth media and incubated for 72 h at 37° C. Cells were washed with 200 µl warm PBS. 100 µl of para-nitrophenyl phosphate (pNPP, 2 mg/ml) in Na acetate buffer pH 5 (NaAc 0.1 M, 0.1% Triton-X-100) was added per well. Cells were incubated for 2 h after which reaction was stopped by addition of 1N NaOH. Absorbance was measured at 405 nm.

For the FMCA assay cells were seeded in the drug-prepared 384-well plates using the pipetting robot Precision 2000 (Bio-Tek Instruments Inc., Winooski, Vt.). The plates were incubated for 72 h and then transferred to an integrated HTS SAIGAN Core System consisting of an ORCA robot (Beckman Coulter) with $CO_2$ incubator (Cytomat 2C, Kendro, Sollentuna, Sweden), dispenser module (Multidrop 384, Titertek, Huntsville, Ala.), washer module (ELx 405, Bio-Tek Instruments Inc), delidding station, plate hotels, barcode reader (Beckman Coulter), liquid handler (Biomek 2000, Beckman Coulter) and a multipurpose reader (FLUOstar Optima, BMG Labtech GmbH, Offenburg, Germany) for automated FMCA. Survival index (SI) is defined as the fluorescence of test wells in percentage of controls with blank values subtracted.

Cell-Cycle Analysis.

For determination of cell cycle HCT-116 cells were treated with b-AP15 or DMSO Cells were harvested by trypsinisation, washed and fixed in 70% ice cold EtOH for 12 h. Cells were re-suspended in staining solution containing propidium iodide (50 µg/ml) and RNAse A (0.5 µg/ml) in PBS. Samples were run on BD FACScalibur. The percentage of cells in each phase of the cell cycle was determined using ModFit software.

In Vivo Tumor Experiments.

Animal experiments were conducted in full accordance with Swedish governmental statutory regulations on animal welfare under permission from local ethical committees. Animals were housed at a max of five per cage and provided with sterile water and food ad libitum. All mice were monitored and weighed daily. For the head and neck carcinoma model a 100-µl cell suspension containing $1\times10^6$ FaDu cells was injected subcutaneously into the right rear flank of the animals. After injection, tumor growth was measured daily with calipers and the tumor volume calculated by the formula $L=W^2=0.44$. When tumors had grown to a size of approximately 200 $mm^3$ (Day 0) mice were randomized to receive either vehicle (n=10) or b-AP15 5 $mg/kg^{-1}$ by subcutaneous injection s.c. (n=15) daily. For the colon carcinoma model, $2.5\times10^6$ HCT-116 colon carcinoma cells stably transfected with Bcl-2 (HCT-116$^{Bcl-2+}$) were inoculated subcutaneously into the right flank of nude mice. One day after inoculation mice were treated with 5 $mg/kg^{-1}$ by intra peritoneal injection (i.p.). Animals were inspected daily to establish the tumor onset and growth. For the lung carcinoma model a 100-µl cell suspension containing $2\times10^5$ Lewis Lung Carcinoma (LLC) cells was injected subcutaneously into the right rear flank of C57/B6 mice. When tumors had grown to a size of approximately 50 mm³ (Day 0) mice were randomized to receive either vehicle (n=4) or b-AP15 5 mg/kg⁻¹ i.p. (n=4) with a treatment cycle consisting of two days treatment followed by two days no treatment (2 days on/2 days off) for two weeks. For the breast carcinoma model a 100-µl cell suspension containing 1×10⁵ 4 TD cells was injected subcutaneously into the right mammary fat pad of BALB/c mice. When tumors had grown to a size approximately 25 mm³ (Day 0), mice were randomized to receive either vehicle (n=5) or b-AP15 2.5 mg/kg⁻¹ i.p. (n=5) with a treatment cycle consisting of one days treatment followed by three days no treatment (1 day on/3 days off) for 3 weeks. In the AML studies female C57BL/6J mice were injected i.v. in the tail vein with 5×10⁵ C1498 AML cells. After eight days mice were randomized to receive either b-AP15 5 mg/kg⁻¹ (n=10) or vehicle (n=10) i.p. for 7 days (day +8 till +14). Nineteen days after malignant cell injection all of the mice were killed and histopathological manifestations of liver, ovary (target organs for this model of tumor) were evaluated and compared between groups. For administration of drug b-AP15 was dissolved in Cremphor EL:PEG 400 (1:1) by heating to give a working concentration of 2 mg/ml. Working stock was 1:10 diluted in 0.9% normal saline immediately prior to injection.

Determination of Caspase-Cleaved CK18 in Mouse Plasma.

For measurement of the apoptosis-related CK18-Asp396 fragment, 12.5 ml of plasma was collected 24 h after last treatment and analyzed using the M30-Apoptosense® assay. Each sample was mixed with 0.4 ml of heterophilic blocking reagent (Scantibodies Laboratory Inc).

Determination of Pulmonary Metastases.

Since the 4T1 cells are resistant to 6-thioguanine, metastases can be determined by culturing homogenized tissue in the presence of 6-thioguanine. For determination of metastatic 4T1 cells the protocol was as described (45). In brief lungs from treated or untreated animals were homogenized and treated with collagenase and elastase. Cells were grown in the presence of 60 µM 6-thioguanine for 2 weeks and the number of metastatic colonies determined by giemsa staining.

Immunostaining.

Tumor sections were de-paraffinized with xylene, rehydrated and then incubated over-night with K-48 ubiquitin or active-caspase 3 (1/500) diluted in 1% (wt/vol) bovine serum albumin and visualized by standard avidin-biotin-peroxidase complex technique (Vector Laboratories). Counterstaining was performed with Mayer's haematoxylin.

Statistical Analyses.

For comparisons of treatment groups, we performed the unpaired t test (Mann-Whitney), repeated measures ANOVA and Kaplan-Meier survival (Mantel-Cox test). All statistical analyses were performed using GraphPad Prism Software (version 5.0). Statistical significance was achieved when P was less than 0.05.

Example 1. b-AP15 Inhibits the Ubiquitin-Proteasome System

CMAP readout of MCF7 cells treated with b-AP15 (1 µM) for 6 h is shown in Table 3.

TABLE 3

CMAP readout of MCF7 cells treated with B-AP15

Figure 1F:
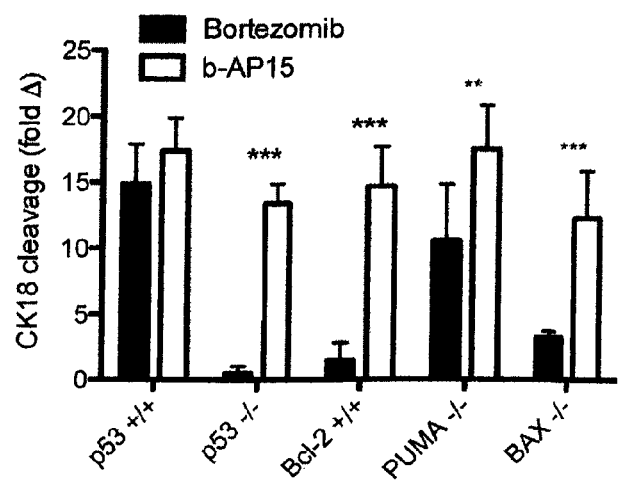

| Rank | Name | Cell | Score |
|---|---|---|---|
| 1 | MG-262 | MCF7 | 1 |
| 2 | 15 Δ prostaglandin J2 | " | 0.999 |
| 3 | Celastrol | " | 0.966 |
| 4 | 15 Δ prostaglandin J2 | " | 0.940 |
| 5 | Withaferin A | " | 0.922 | b-AP15 inhibits degradation of ubiquitin-tagged YFP in a proteasome reporter cell line (FIG. 1a). Levels of $^{UbG76V}$-YFP accumulation were determined by flow cytometry and immunoblotting; immunoblot of ubiquitin conjugation in HCT-116 cells treated with b-AP15 (1 µM) or bortezomib (100 nM) (FIG. 1b). Immunoblot of ubiquitin conjugates, caspase 3 activation PARP cleavage, p53, $P21^{Cip1}$ and $p^{Kip1}$ in HCT-116 cells following 24 h treatment with the indicated concentrations of b-AP15 (FIG. 1c). Immunoblot of ODC-1 levels in HCT-116 cells following treatment with bortezomib (100 mM or b-Ap15 (1 µM) (FIG. 1d); values represent quantified optical density units of ODC-1 normalized to β-actin. Cell cycle profiles of b-AP15 treated HCT-116 cells (FIG. 1e); cells were analyzed by propidium iodide staining and flow cytometry. Levels of caspase activity in isogenic HCT-116 cells as determined by ELISA for caspase cleaved cytokeratin-18 (CK18-Asp398) following treatment with bortezomib (100 nM) or b-AP15 (1 µM) ('P=0.01, *'P=0.001) (FIG. 1f).

Figure 2E:
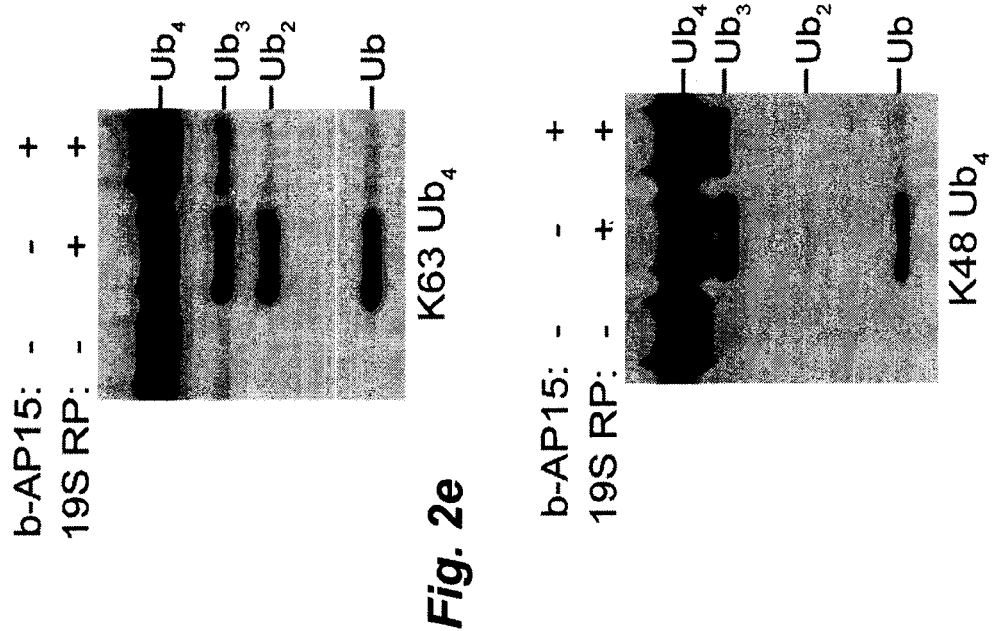
Figure 2D:
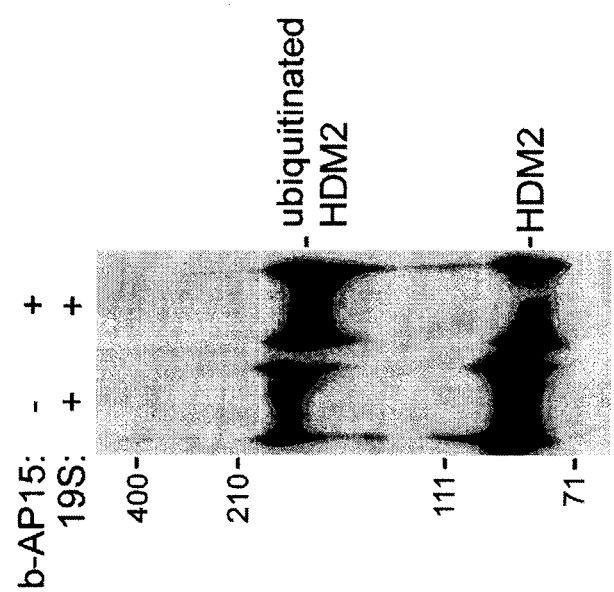

Example 2 b-AP15 inhibits deubiquitination by the 19S RP. Inhibition of Ub-AMC cleavage by 19S RP or 26S proteasomes following treatment with b-AP15; ubiquitin aldehyde (Uba1), a general DUB inhibitor, was included as a control (FIG. 2a). Immunoblot of 19S RP mediated cleavage of Ub-GFP (FIG. 2b); 19S RP were pre-treated with DMSO or indicated concentrations of b-AP15 followed by addition of recombinant Ub-GFP as a DUB substrate. Kinetics of 19S RP Ub-GFP cleavage following b-AP15 (50 µM) treatment (FIG. 2c). b-AP15 inhibits deubiquitination of Hdm2 (FIG. 2d); ubiquitinated Hdm2 was added to DMSO or b-AP15 (50 µM) treated 19S RP followed by immunoblotting. Ubiquitin chain disassembly reactions of K63/K48 linked ubiquitin tetramers by 19S RP following treatment with DMSO or b-AP15 (50 µM) (FIG. 2e).

Example 3. b-AP15 Inhibits the 19S RP DUBs UCHL5 and USP14

19S RP were pre-treated with DMSO, NEM (10 mM) b-AP15 (50 µM) (FIG. 3a) or TPEN (250 µM) (FIG. 3b) followed by addition of Ub-GFP and immunoblotting with anti-GFP antibodies. Active site directed labelling of proteasomal DUBs (FIG. 3c); purified 19S or 26S proteasomes were pre-treated with DMSO, NEM or bAP15 followed by labeling with HA-UbVS and immunoblotting. Immunoblot of HCT116 cells treated with b-AP15 (1 µM) for 3 h (FIG. 3d); DUBs from whole cell lysates were labelled with HA-UbVS followed by SDS-PAGE and immunoblotting with indicated antibodies.

Example 4. b-AP15 Inhibits Tumor Growth In Vivo

SCID mice bearing FaDu human tumor xenografts were randomized at tumor take (200 mm³) and treated by daily subcutaneous injection with either vehicle (n=10) or 5 mg kg$^{-1}$ b-AP15 (n=15) for 10 days. Mean tumor volume ±SEM shown (\*\*\*P=<0.001) (FIG. 4a). Total levels of tumor derived CK18 and caspase cleaved (CK 18-Asp396) in circulation following b-AP15 treatment (\*\*P=0.01) (FIG. 4b). Disease free survival of nude mice challenged with HCT-116$^{Bcl-2+}$ cells (FIG. 4c). Mice were treated with vehicle (n=6) or 5 mg kg$^{-1}$ b-AP15 (n=6) 4-5 times weekly for 3 weeks and monitored for tumor onset (log-rank, P=0.0136, hazard ratio=7.9). C57BL/6J mice bearing syngenic lung carcinoma (LLC) tumors were treated with either vehicle (n=4) of 5 mg kg b-AP15 (n=4) in a one day on/two days off cycle (FIG. 4d); mean tumor volume ±SEM shown (P=<0.01). BALB/c mice bearing orthotopic breast carcinomas (4T1) were treated with either vehicle (n=5) or 2.5 mg kg$^{-1}$ b-AP15 (n=5) in a one day on/three days off cycle (FIG. 4e); mean tumor volume ±SEM shown (\*\*P=<0.01). Box and whisker plots of pulmonary metastatic colonies from vehicle or b-AP15 treated 4T1 breast carcinomas (FIG. 4f); boxes represent upper and lower quartiles and median, whiskers show maximum and minimum values. Representative immunohistochemical staining for K48-linked ubiquitin accumulation and cleaved caspase-3 in vehicle and b-AP15 treated 4T1 tumors, original magnification ×20 (FIG. 4g). AML infiltration in liver and ovary of vehicle and b-AP15 treated mice (FIG. 4h). Liver of vehicle treated mice showed invasion of leukemic blasts along with glycogen depletion and non-specific hemorrhage. Ovary section of vehicle treated mice showed massive invasion of leukemic blasts and interstitial bleeding. In contrast, liver and ovary from b-AP15 treated mice showed few infiltrated blasts and normal morphology (original magnification ×20).

Example 5. b-AP15 does not Induce DNA Damage

Figure 5:
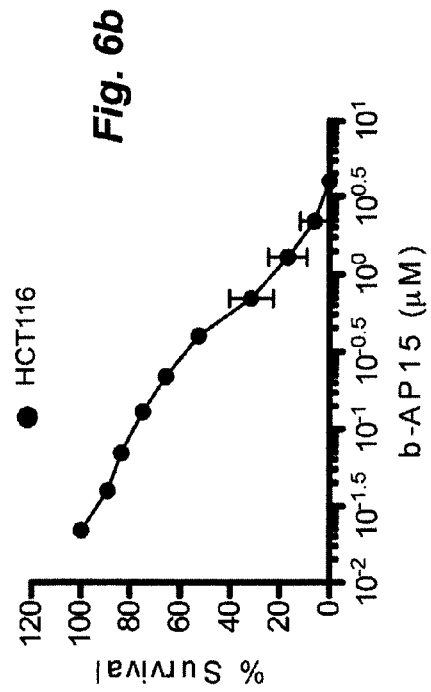
FIG. 5 Absence of DNA damage potentially caused by b-AP15.

HCT-116 cells were treated with b-AP15 or doxorubicin (100 nM, as a positive control for genotoxic stress for 18 h) (FIG. 5). Cell lysates were immuno-blotted with antibodies for phosphorylated p53 and histone H2 Ax marker for DNA damage of for total levels of p53 and β-actin as loading controls.

Figure 6B:
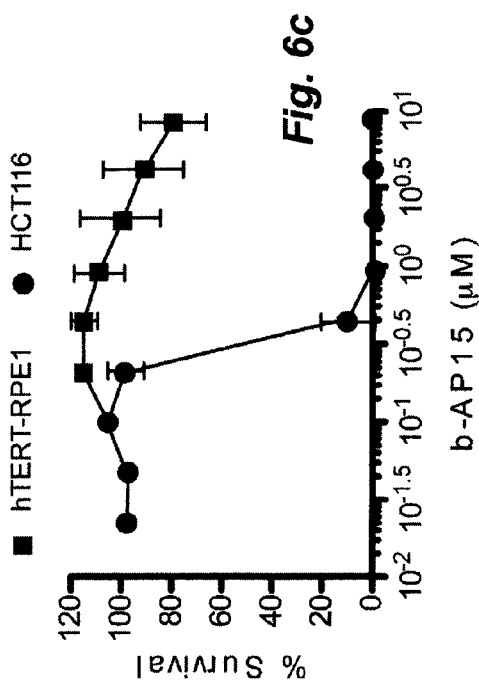
FIGS. 6a-6f Induction by b-AP-15 of apoptosis and inhibition of cell survival of HCT-116 cells.
Figure 6C:
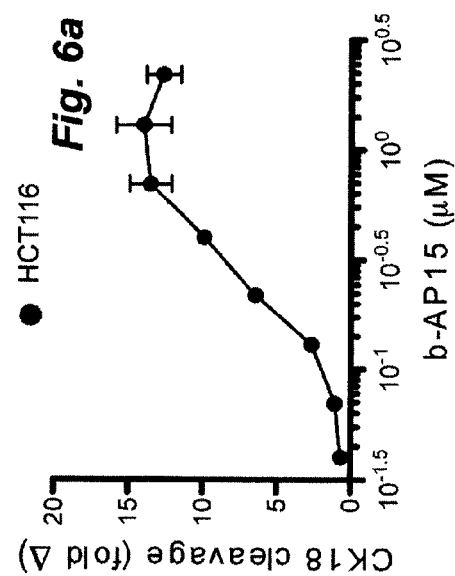
Figure 6A:
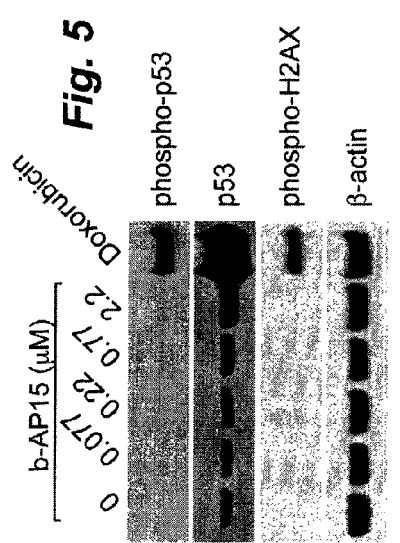
Figure 6F:
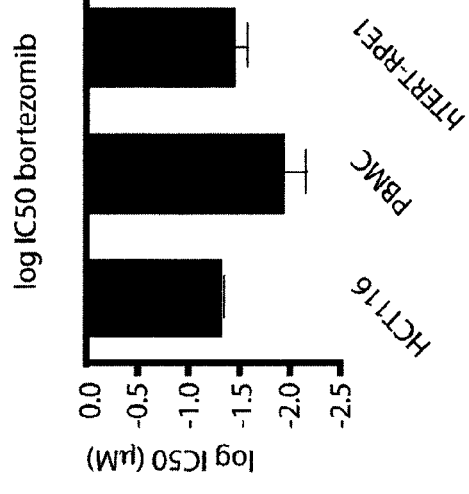
Figure 6D:
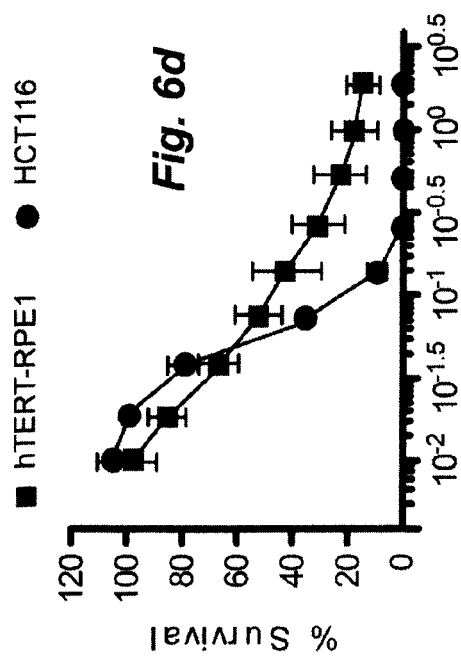
Figure 6E:
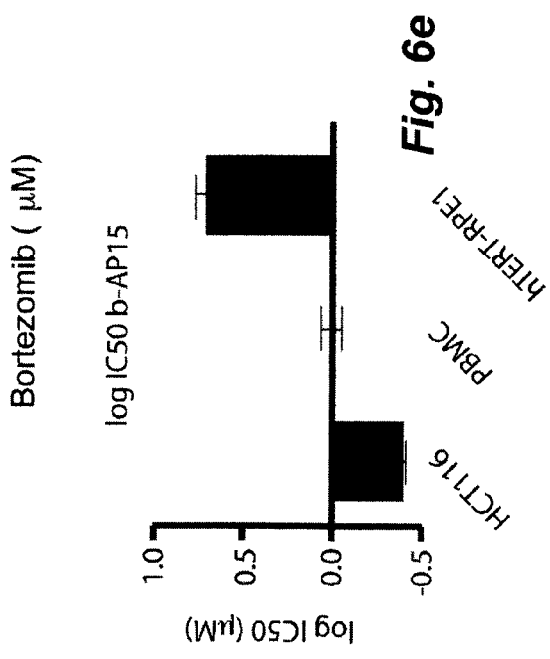

Example 6. b-AP15 Induces Apoptosis and Inhibits Cell Survival of HCT-116 Cells Whereas PBMC (Peripheral Blood Mononuclear Cells) and Immortalized hTERT-RPE1 are Less Sensitive HCT-116 cells were treated with increasing concentrations of b-AP15 for 24 h and the levels of apoptosis were determined by measuring the levels of caspase cleaved cytokeratin-18 (CK18) by ELISA assay (FIG. 6a). HCT-116 cells were treated with increasing concentrations of b-AP15 for 48 h). Cell viability was determined by acid-phosphatase activity assay. Mean values ±s.d. shown (FIG. 6b). HCT-116 or hTERT-REP1 cells were treated with increasing concentrations of b-AP15 for 72 h followed by analysis of cytotoxicity using the FMCA method (44) (FIG. 6c). HCT-116 or hTERT-REP1 cells were treated with increasing concentrations of bortezomib for 72 h followed by analysis of cytotoxicity using the FMCA method (FIG. 6d). HTERT-RPE1 is an immortalized human retinal pigment epithelial cell line (39). IC50 was determined from log concentration/effect curves in Graph Pad Prism (GraphPad Software Inc. CA, USA) using non-linear regression analysis (four parameter model with variable Hill slope) (FIGS. 6e, 6f). Concentration/response curves were generated in two-fold dilutions at eight concentrations of b-AP15 and bortezomib in triplicate using the FMCA assay. The results are expressed as log IC50+SD from four or five independent experiments (HCT-116, n=5; PBMC, n=4; hTERT-RPE1, n=5).

Example 7. Dose Response Curves of Apoptosis Induction in Isogenic Clones of HCT-116 Cells HCT-116 cells were treated with increasing concentrations of bortezomib or b-AP15 for 24 h and the levels of apoptosis were determined by measuring the levels of caspase cleaved cytokeratin-18 (CK-18) by ELISA assay (Mean fold change ±s.d, n=4) (FIG. 7).

Example 8. b-AP15 does not Inhibit the Proteolytic Activities of the Proteasome

20S CP (2 nM) was pretreated with DMSO, b-AP15 (50 µM) or bortezomib (100 nM) for 5 min in assay buffer (25 mM HEPES, 0.5 mM EDTA, 0.03% SDS) followed by the addition of 100 µM of the fluorogenic substrates Suc-LLVY-AMC, Z-LLE-AMC or Boc-LRR-AMC for analysis of proteasome chymotrypsin-like, caspase-like and trypsin-like activities, respectively (FIG. 8a). 26S proteasomes (2 nM) in assay buffer (25 mM HEPES, 50 mM NaCl, 1 mM MgCl$_2$, 2 mM ATP, 1 mM DTT) were treated as in the experiment illustrated in FIG. 8a (FIG. 8b). Values represent fold cleavage in relative fluorescent units.

Figure 9A:
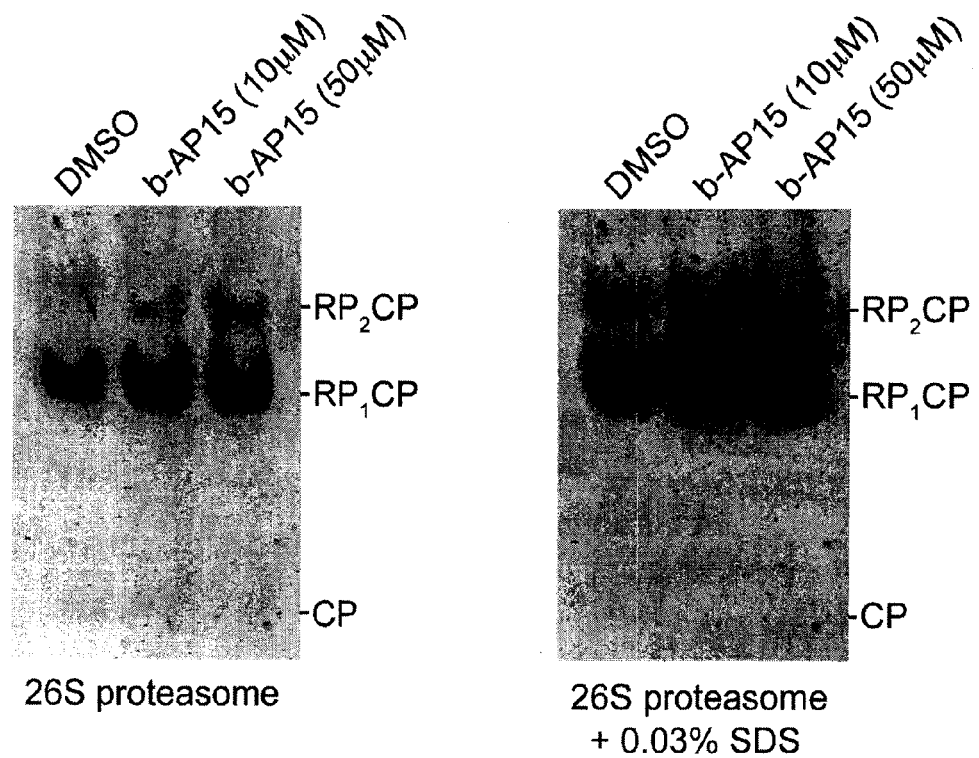
FIGS. 9a, 9b Absence of dissociation of 19S and 20S particles potentially caused by b-AP15 or alteration of ubiquitin binding caused by b-AP15.
Figure 9B:
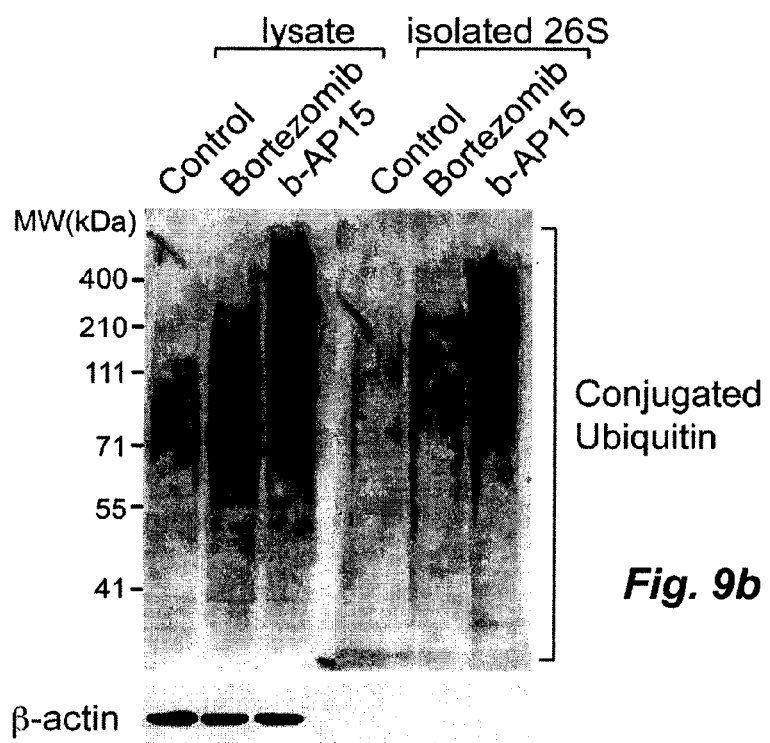

Example 9. b-AP15 does not Cause Dissociation of 19S and 20S Particles or Alter Ubiquitin Binding Substrate overlay assay of b-AP15 treated proteasomes (FIG. 9a). Purified 26 S proteasome was treated with b-AP15 (10 µM or 50 µM) separated by native gel electrophoresis and assayed for proteolytic activity using Suc-LLVY-AMC as a fluorogenic substrate for peptidase activity. Analysis of the gels showed the presence of doubly (RP$_2$CP) and singly (RP$_1$CP) capped proteasomes in both control and b-AP15 lanes. The addition of 0.03% SDS did not reveal an increase in the presence of uncapped 20S core particles. b-AP15 does not alter proteasome-ubiquitin binding activity (FIG. 9b). HCT-116 cells were treated with bortezomib (100 nNM) or b-AP15 (1 µM), and the proteasomes were affinity purified. Levels of associated polyubiquitin were determined by immunoblotting.

Example 10. b-AP15 is not a General DUB Inhibitor

Figure 10:
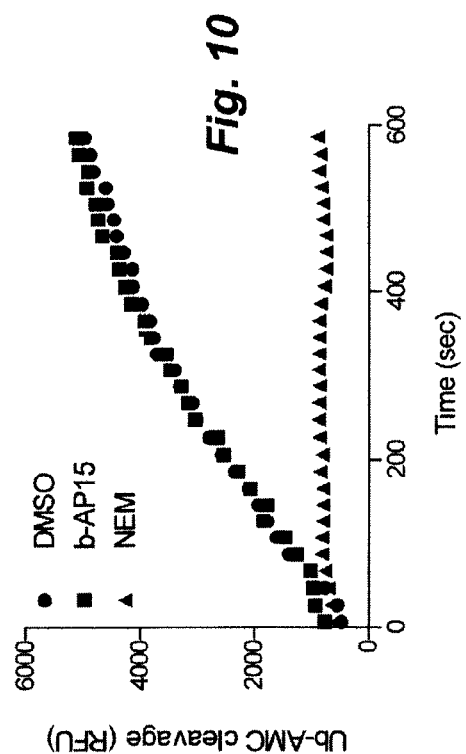
FIG. 10 b-AP15 not being a general DUB inhibitor.

HTC-116 cells were treated for 3 h with b-AP15 (1 µM) (FIG. 10). Lysates treated with 10 mM N-ethylmaleimide (NEM) were included as a control for total DUB inhibition. DUB activity was determined from cell lysates by measuring cleavage of the fluorogenic substrate ubiquitin-7-amido-4-methylcoumarin (Ub-AMC).

Example 11. Biochemical Characterization of b-AP15 Binding

Dose response of b-AP15 (FIG. 11a): Purified 19S proteasomes (5 nM) were treated with indicated concentrations of b-AP15, and DUB activity was determined by detection of Ub-AMC cleavage. The IC50 value (2.1±0.411 µM) was determined from log concentration curves in Graph Pad Prism using non-linear regression analysis (mean values ±SD, n=3). It should be noted that IC50 observed in cell-free assays is somewhat higher than that observed in cells, probably due to the hydrophobicity of b-AP15 (X Log P=3.3) resulting in enrichment of the compound in cells (11). Reversibility of b-AP15 inhibition (FIG. 1b): The reversibility of inhibition was determined by measuring recovery of DUB activity after rapid dilution of the enzyme/b-AP15 complex. A reaction mix containing 50 times the 19S concentration normally used in reactions (250 mM) and 10 times the calculated IC50 value for b-AP15 (25 µM) was incubated on ice for 15 min followed by a 50-fold dilution in reaction buffer to give a final concentration of 5 nM for 19'S and 0.5 µM for b-AP15. The linear reaction curves of Ub-AMC cleavage show that b-AP15 is a reversible inhibitor. Determination of whether b-AP15 reacts non-specifically with cysteine residues (FIG. 11c). 19S (5 nM) was treated with b-AP15 (10 µM) or b-Ap15 (10 µM) mixed with reduced glutathione (GSH (2 mM). The presence of glutathione did not reduce b-AP15 mediated inhibition of 19S DUB activity.

Example 12. b-AP15 is not a General DUB Inhibitor

HCT-116 cells were treated for 3 h with b-AP15 (1 µM) and the proteasomes were affinity purified (FIG. 12a). Proteasome DUB activity is expressed as cleavage of Ub-AMC/suc-LLVY-AMC to normalize for proteasome recovery (P=0.012, unpaired t-test, two tailed). b-AP15 does not inhibit non-proteasomal DUBs (FIG. 12b). Recombinant non-proteosomal DUBs were treated with b-AP15 and % activity determined. Cell lysates from 293T and HeLa cells were treated with b-AP15 (50 µM) followed by active labelling with HA-UbVS (FIG. 12c). All samples were run on SD-PAGE followed by immunoblotting with α-HA antibodies.

Figure 13:
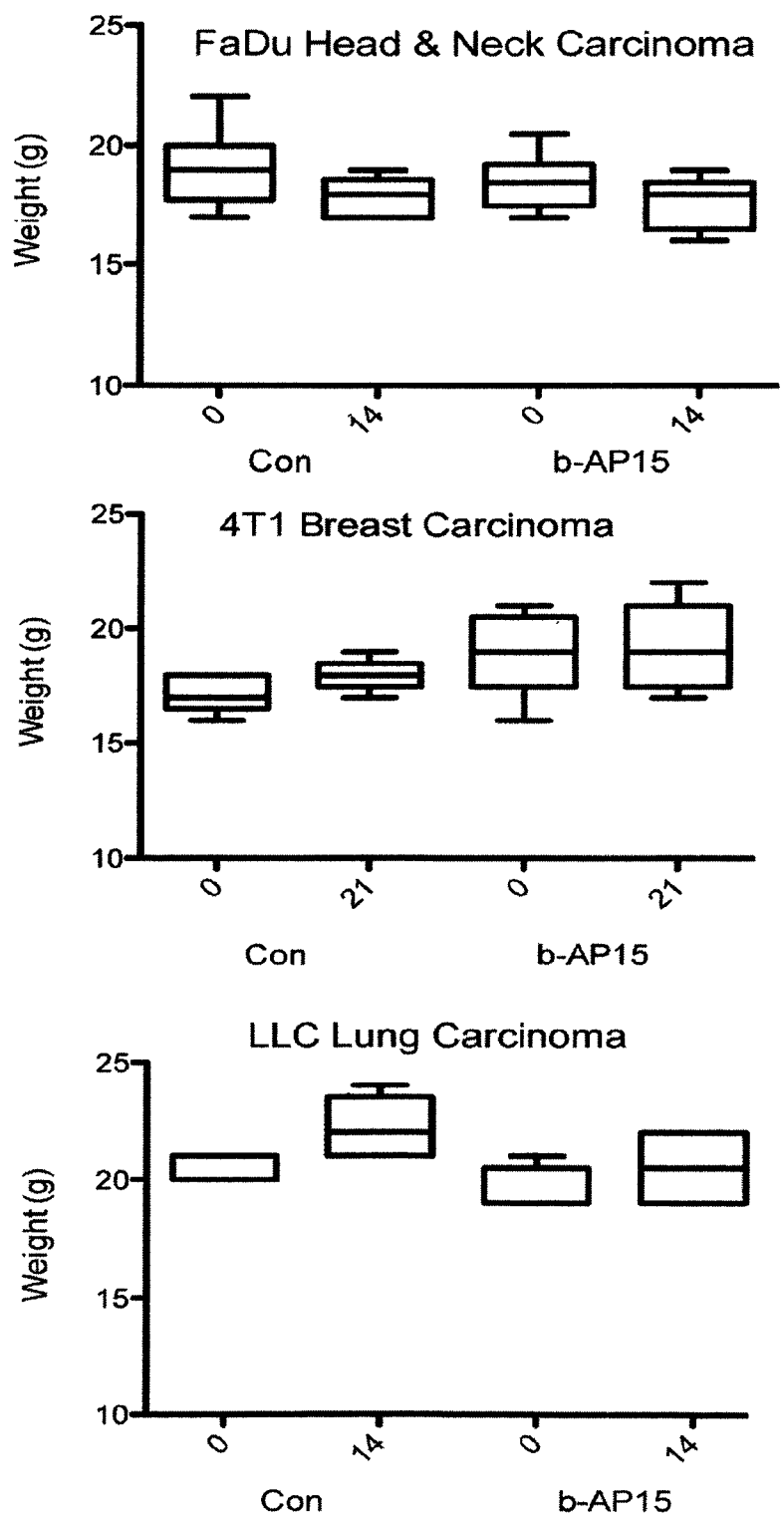
FIG. 13 Absence of significant alteration of animal weight by treatment with b-AP15.

Example 13. b-AP15 Treatment does not Significantly Alter Animal Weight (FIG. 13)

The difference in weight at the start and the endpoint between control and treated animals for the xenografts shown in FIG. 4 was: FaDu, −1.3%; LLC, +2.1%; 4T1+ 5.8%. Boxes represent the upper and lower quartiles and median, whiskers show maximum and minimum values.

Figure 14:
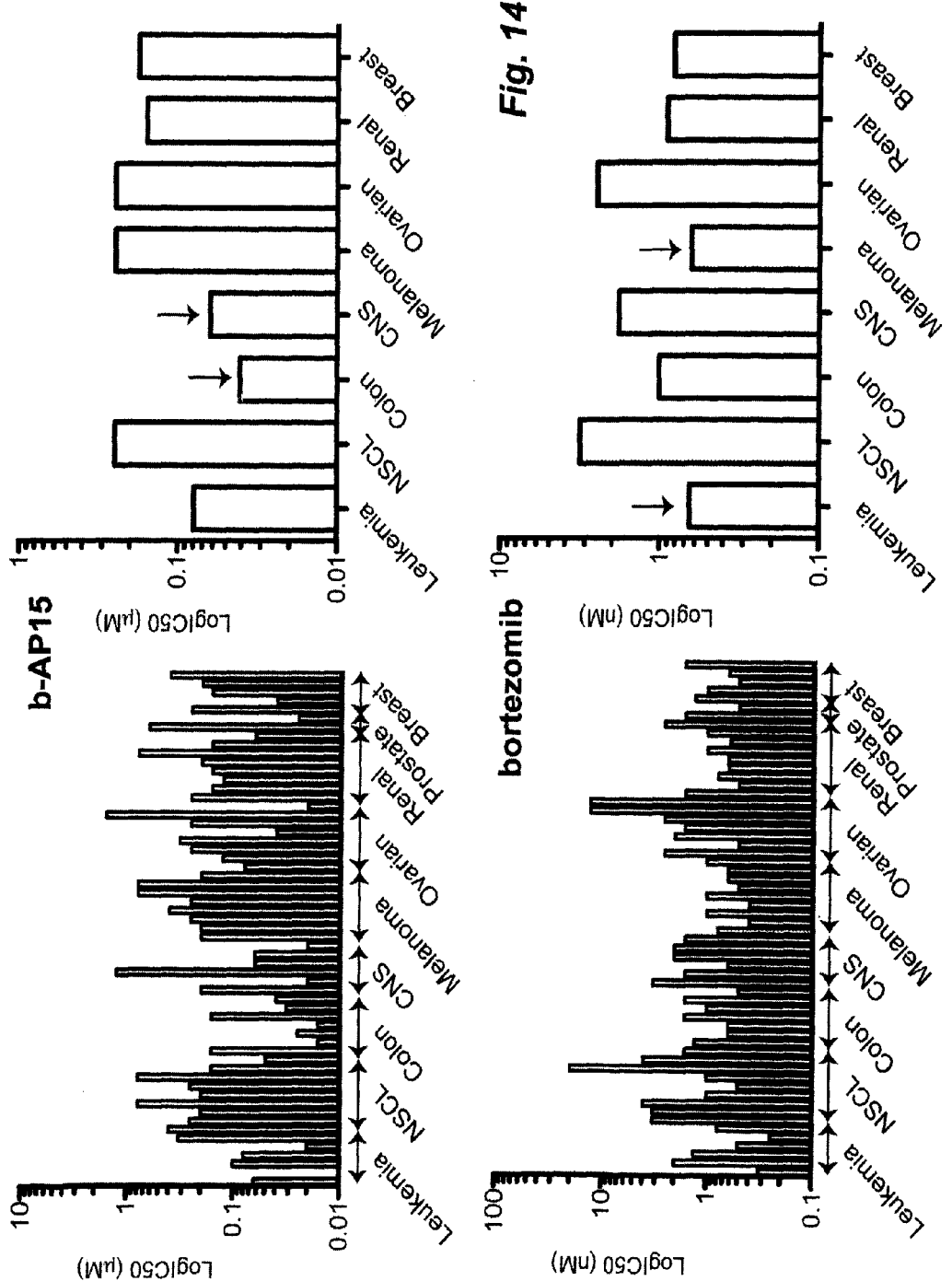
FIG. 14 Sensitivity of cell lines in the NC160 cell line to b-AP15 and bortezomib.

Example 14. Sensitivity of Cell Lines in the NC160 Cell Line to b-AP15 and Bortezomib (FIG. 14)

Shown are IC50 values for individual cell lines (left hand graphs) and median IC50 for each tumor type (right hand graphs). Data have been taken from www.dtp.nci.nih.gov. Arrows indicate the two most sensitive tumor cell types for each drug.

Example 15. Expression of Chaperone Genes Observed in bAP15-Treated Cells

Expression of chaperone genes observed in bAP15-treated cells (Table 1) is indicative of induction of a proteotoxic response.

TABLE 1

Induction of chaperone expression after b-AP15 treatment

| Probe Set ID | Gene Title | Gene Symbol | Expression values b-AP15 | Expression values Vehicle | Fold change |
|---|---|---|---|---|---|
| 117_at | heat shock 70 kDa protein 6 (HSP70B') | HSPA6 | 24149 | 33 | 725 |
| 225061_at | DnaJ (Hsp40) homolog, A4 | DNAJA4 | 21103 | 711 | 30 |
| 203810_at | DnaJ (Hsp40) homolog, B4 | DNAJB4 | 1955 | 123 | 16 |
| 205543_at | heat shock 70 kDa protein 4-like | HSPA4L | 5452 | 406 | 13 |
| 200666_s_at | DnaJ (Hsp40) homolog, B1 | DNAJB1 | 33900 | 5251 | 6 |
| 241716_at | heat shock 60 kDa protein 1 | HSPD1 | 487 | 77 | 6 |
| 203811_s_at | DnaJ (Hsp40) homolog, B4 | DNAJB4 | 960 | 178 | 5 |
| 202581_at | heat shock 70 kDa protein 1B | HSPA1B | 31068 | 6382 | 5 |
| 206976_s_at | heat shock 105 kDa/110 kDa protein 1 | HSPH1 | 40974 | 8427 | 5 |
| 211016_x_at | heat shock 70 kDa protein 4 | HSPA4 | 1803 | 422 | 4 |
| 202843_at | DnaJ (Hsp40) homolog, B9 | DNAJB9 | 1879 | 449 | 4 |
| 200880_at | DnaJ (Hsp40) homolog, A1 | DNAJA1 | 19970 | 4872 | 4 |
| 200800_s_at | heat shock 70 kDa protein 1A | HSPA1A | 57478 | 14352 | 4 |

Further analysis by quantitative PCR showed that b-AP15 induces a stronger HSPA6 (Hsp70B'), HSPA1B and DNAJB1 (Hsp40) expression than bortezomib (Table 2). HSPA6, which is known to be induced in response to accumulation of damaged proteins (35), was induced >1000-fold by b-AP15. These findings indicate that high molecular weight ubiquitin substrate complexes accumulating as a result of DUB inhibition can generate strong cytotoxicity that is insensitive to Bcl-2 over-expression.

TABLE 2

Quantitation of chaperone gene induction.

| Gene Title | Gene Symbol | Fold induction[#] b-AP15 | Fold induction[#] bortezomib |
|---|---|---|---|
| heat shock 70 kDa protein 6 (Hsp70B') | HSPA6 | 1550 | 60 |
| heat shock 70 kDa protein 1B (Hspa1b) | HSPA1B | 21 | 12 |
| DnaJ homolog, B1 (Hsp40B1) | DNAJB1 | 22 | 5 |

[#]HCT116 cells were treated with IC90 concentrations of b-AP15 or bortezomib and mRNA levels were determined after reverse transcription and real time PCR. Fold induction is expressed as fold untreated control. The experiment was repeated with similar results.

The cellular response to b-AP15 is not only distinct from that of bortezomib in regard of involvement of apoptosis regulators but also in regard of the sensitivity of tumor cell lines in the NCI-60 cell line panel (http://dtp.nci.nih.gov).

Inhibitors of 19S RP DUB activity should display a therapeutic spectrum different from that of inhibitors of 20S enzymatic activity, and therefore expand the arsenal of therapy options in oncology.

REFERENCES

1. Masdehors, P et al., *Increased sensitivity of CLL-derived lymphocytes to apoptotic death activation by the proteasome-specific inhibitor lactacystin*. Br J Haematol 105, 752-757, doi:bjh1388 [pii] (1999).
2. DeMartino, G N et al., *PA700, an ATP-dependent activator of the 20 S proteasome, is an ATPase containing multiple members of a nucleotide binding protein family*. J Biol Chem 69, 20878-20884, http://www.ncbi.nlm.nih.gov/entrez/query.fcgi?cmd=Retrieve&db=PubMed&dopt=Citation&list_uids=8063704 (1994) (1994).
3. Rechsteiner, M et al., *The multicatalytic and 26 S proteases*. J Biol Chem 268, 6065-6068, http://www.ncbi.nlm.nih.gov/entrez/query.fcgi?cmd=Retrieve&db=PubMed&dopt=Citation&list_uids=8454582 (1993).
4. Adams, J & Kauffman, M, *Development of the proteasome inhibitor Velcade (Bortezomib)*. Cancer Invest 22, 304-311, http://www.ncbi.nlm.nih.gov/entrez/query.fcgi?cmd=Retrieve&db=PubMed&dopt=Citation&list_uids=15199612 (2004).
5. Erdal, H et al., *Induction of lysosomal membrane permeabilization by compounds that activate p53-independent apoptosis*. Proc Natl Acad Sci USA 102, 192-197, doi:0408592102 [pii]10.1073/pnas.0408592102 (2005).
6. Berndtsson, M et al., *Induction of the lysosomal apoptosis pathway by inhibitors of the ubiquitin-proteasome system*. Int J Cancer 124, 1463-1469, doi:10.1002/ijc.24004 (2009).
7. Lamb, J et al., *The Connectivity Map: using gene-expression signatures to connect small molecules, genes, and disease*. Science 313, 1929-1935, doi:313/5795/1929 [pii]10.1126/science.1132939 (2006).
8. Adams, J et al., *Potent and selective inhibitors of the proteasome: dipeptidyl boronic acids*. Bioorg Med Chem Lett 8, 333-338 333-338, doi:S0960894X98000298 [pii] (1998).
9. Shibata, T et al., *An endogenous electrophile that modulates the regulatory mechanism of protein turnover: inhibitory effects of 15-deoxy-Delta 12,14-prostaglandin J2 on proteasome*. Biochemistry 42, 13960-13968, doi: 10.1021/bi035215a (2003).
10. Yang, H et al., *Celastrol, a triterpene extracted from the Chinese "Thunder of God Vine," is a potent proteasome inhibitor and suppresses human prostate cancer growth in nude mice*. Cancer Res 66, 4758-4765 4758-4765, doi: 66/9/4758 [pii]10.1158/0008-5472.CAN05-4529 (2006).
11. Yang, H et al., *The tumor proteasome is a primary target for the natural anticancer compound Withaferin A isolated from "Indian winter cherry"*. Mol Pharmacol 71, 426-437, doi:mol.106.030015 [pii]10.1124/mol.106.030015 (2007).
12. Menendez-Benito, V et al., *Endoplasmic reticulum stress compromises the ubiquitin-proteasome system*. Hum Mol Genet 14, 2787-2799, doi:ddi312 [pii]10.1093/hmg/ddi312 (2005).
13. Mimnaugh, E G et al., *Rapid deubiquitination of nucleosomal histones in human tumor cells caused by proteasome inhibitors and stress response inducers: effects on replication, transcription, translation, and the cellular stress response*. Biochemistry 36, 14418-14429, doi: 10.1021/bi970998jbi970998j [pii] (1997).
14. Shieh, S Y et al., *DNA damage-induced phosphorylation of p53 alleviates inhibition by MDM2*. Cell 91, 325-334, doi:S0092-8674(00)80416-X [pii] (1997).
15. Rogakou, E P et al., *DNA double-stranded breaks induce histone H2AX phosphorylation on serine 139*. J Biol Chem 273, http://www.ncbi.nlm.nih.gov/entrez/query.fcgi?cmd=Retrieve&db=PubMed&dopt=Citation&list_uids=9488723 (1998).
16. Ling, X et al., *Cancer cell sensitivity to bortezomib is associated with surviving expression and p53 status but not cancer cell types*. J Exp Clin Cancer Res 29, 8 (2010).
17. Paoluzzi, L et al., *The BH3-only mimetic ABT-737 synergizes the antineoplastic activity of proteasome inhibitors in lymphoid malignancies*. Blood 112, 2906-2916 (2008).
18. Borissenko, L & Groll, M, *20S proteasome and its inhibitors: crystallographic knowledge for drug development*. Chem Rev 107, 687-717, doi:10.1021/cr0502504 (2007).
19. Eytan, E et al., *ATP-dependent incorporation of 20S protease into the 26S complex that degrades proteins conjugated to ubiquitin*. Proc Natl Acad Sci USA 86, 7751-7755, http://www.ncbi.nlm.nih.gov/entrez/query.fcgi?cmd=Retrieve&db=PubMed&dopt=Citation&list_uids=2554287 (1989).
20. Chu-Ping, M et al., *Identification, purification, and characterization of a high molecular weight, ATP-dependent activator (PA700) of the 20 S proteasome*. J Biol Chem 269, http://www.ncbi.nlm.nih.gov/entrez/query.fcgi?cmd=Retrieve&db=PubMed&dopt=Citation&list_uids=8106396 (1994).
21. Mullally, J E & Fitzpatrick, F A, *Pharmacophore model for novel inhibitors of ubiquitin isopeptidases that induce p53-independent cell death*. Mol Pharmacol 62, http://www.ncbi.nlm.nih.gov/entrez/query.fcgi?cmd=Retrieve&db=PubMed&dopt=Citation&list_uids=12130688 (2002).
22. Guterman, A & Glickman, M H, *Complementary roles for Rpn11 and Ubp6 in deubiquitination and proteolysis by the proteasome*. J Biol Chem 279, 17291738, doi: 10.1074/jbc.M307050200 [pii] (2004).
23. Glickman, M H & Ciechanover, A, *The ubiquitin-proteasome proteolytic pathway: destruction for the sake of construction*. Physiol Rev 82, 373-428, doi:10.1152/physrev.00027.2001 (2002).
24. Hofmann, R M & Pickart, C M et al., *Noncanonical MMS2-encoded ubiquitin conjugating enzyme functions in assembly of novel polyubiquitin chains for DNA repair*. Cell 96, 645-653, doi:S0092-8674(00)80575-9 [pii] (1999).
25. Vong, Q P et al., *Chromosome alignment and segregation regulated by ubiquitination of surviving cells*. Science 310, 1499-1504, doi:310/5753/1499 [pii]10.1126/science.1120160 (2005).
26. Borodovsky, A et al., *A novel active site-directed probe specific for deubiquitylating enzymes reveals proteasome association of USP14*. EMBO J 20, 5187-5196, doi: 10.1093/emboj/20.18.5187 (2001).
27. Lam, Y A et al., *Specificity of the ubiquitin isopeptidase in the PA700 regulatory complex of 26 S proteasomes*. J Biol Chem 272, 28438-28446, http://www.ncbi.nlm.nih.gov/entrez/query.fcgi?cmd=Retrieve&db=PubMed&dopt=Citation&list_uids=9353303 (1997).
28. Verma, R et al., *Role of Rpn11 metalloprotease in deubiquitination and degradation by the 26S proteasome*. Science 298, 611-615, doi:10.1126/science.10758981075898 [pii] (2002).

29. Yao, T & Cohen, R E, *A cryptic protease couples deubiquitination and degradation by the proteasome.* Nature 419, 403-407, doi:10.1038/nature01071nature01071 [pii] (2002).
30. Olofsson, M H et al., *Specific demonstration of drug-induced tumour cell apoptosis in human xenograft models using a plasma biomarker.* Cancer Biomarkers 5, 117-125, http://www.ncbi.nlm.nih.gov/pubmed/19407366 (2009).
31. Kramer, G et al., *Differentiation between cell death modes using measurements of different soluble forms of extracellular cytokeratin 18.* Cancer Res 64, 1751-1756 http://www.ncbi.nlm.nih.gov/entrez/query.fcgi?cmd=Retrieve&db=PubMed&dopt=Citation&list_uids=14996736 (2004).
32. Reyes-Turcu, F E et al., *Regulation and cellular roles of ubiquitin-specific deubiquitinating enzymes.* Annu Rev Biochem 78, 363-397, http://www.ncbi.nlm.nih.gov/entrez/query.fcgi?cmd=Retrieve&db=PubMed&dopt=Citation&list_uids=19489724 (2009).
33. Koulich, E et al., *Relative structural and functional roles of multiple deubiquitylating proteins associated with mammalian 26S proteasome.* Mol Biol Cell 19, 1072-1082, doi:E07-10-1040 [pii]10.1091/mbc.E07-10-1040 (2008).
34. Fennell, D A et al., *BCL-2 family regulation by the 20S proteasome inhibitor bortezomib.* Oncogene 27, 1189-1197, http://www.ncbi.nlm.nih.gov/entrez/query.fcgi?cmd=Retrieve&db=PubMed&dopt=Citation&list_uids=17828309 (2008).
35. Noonan, E J et al., *Hsp70B' regulation and function.* Cell Stress Chaperones 12, 393-402, http://www.ncbi.nlm.nih.gov/entrez/query.fcgi?cmd=Retrieve&db=PubMed&dopt=Citation&list_uids=18229458 (2007).
36. Bunz, F. et al., *Requirement for p53 and p21 to sustain G2 arrest after DNA damage.* Science 282, 1497-1501 (1998).
37. Pietenpol, J A et al., *Paradoxical inhibition of solid tumor cell growth by bcl2.* Cancer Res 54, 3714-3717 (1994).
38. Menendez-Benito, V et al., *Endoplasmic reticulum stress compromises the ubiquitin-proteasome system.* Hum Mol Genet 14, 2787-2799, doi:ddi312 [pii]10.1093/hmg/ddi312 (2005).
39. Bodnar, A G et al., *Extension of life-span by introduction of telomerase into normal human cells.* Science 279, 349-352 (1998).
40. Lamb, J et al., *The Connectivity Map: using gene-expression signatures to connect small molecules, genes, and disease.* Science 313, 1929-1935, doi:313/5795/1929 [pii] 10.1126/science.1132939 (2006).
41. Elsasser, S et al., *Characterization of the proteasome using native gel electrophoresis.* Methods Enzymol 398, 353-363, doi:S0076-6879(05)98029-4 [pii]10.1016/S0076-6879(05)98029-4 (2005).
42. Guterman, A & Glickman, M H, *Complementary roles for Rpn11 and Ubp6 in deubiquitination and proteolysis by the proteasome.* J Biol Chem 279, 1729-1738, doi:10.1074/jbc.M307050200M307050200 [pii] (2004).
43. Hagg, M et al., *A novel high-through-put assay for screening of pro-apoptotic drugs.* Invest New Drugs 20, 253-259 (2002).
44. Lindhagen, E et al., *The fluorometric microculture cytotoxicity assay.* Nat Protoc 3, 1364-1369, doi: nprot.2008.114 [pii]10.1038/nprot.2008.114 (2008).
45. Pulaski, B A & Ostrand-Rosenberg, S, *Mouse 4T1 breast tumor model.* Curr Protoc Immunol Chapter 20, Unit 20 22, doi:10.1002/0471142735.im2002s39 (2001).
46. Sawada, G. A. et al., *Increased lipophilicity and subsequent cell partitioning decrease passive transcellular diffusion of novel, highly lipophilic antioxidants.* J Pharmacol Exp Ther 288, 1317-1326 (1999).

The invention claimed is:
1. A method for screening a compound to determine the compound's proteasome deubiquitinating inhibitor activity, the method comprising:
(a) contacting the compound with human 19S regulatory particles (19S RP) of 26S proteasome in the presence of deubiquitinating (DUB) enzymes UCHL5 and USF14, and determining if the compound inhibits UCHL5 and USF14 activities as compared with UCHL5 and USP14 activities in the presence of human 19 S RP of 26S proteasome and the absence of the compound; and
(b) contacting the compound with human 19S RP of 26S proteasome in the presence of one or more non-proteasomal associated DUB enzymes, and determining if the compound inhibits activities of the one or more non-proteasomal associated DUB enzymes as compared with activities of the one or more non-proteasomal associated DUB enzymes in the presence of human 19 S RP of 26S proteasome and the absence of the compound,
wherein inhibition of UCHL5 and USP14 activities indicates that the compound is a proteasome deubiquitinating inhibitor and wherein non-inhibition of activities of the one or more non-proteasomal associated DUB enzymes indicates that the compound is selective for inhibition of the DUB enzymes UCHL5 and USP14.
2. The method of claim 1, wherein the one or more non-proteasomal associated DUB enzymes comprise at least one member selected from the group consisting of UCHL1, UCHL3, USP2, USP7, USP8.
3. The method of claim 1, wherein the determination of the inhibition of UCHL5 and USP14 activities is conducted with an assay performed with human 19S RP and ubiquitin-AMC or HA-ubiquitin vinyl sulfone as a substrate for measuring deubiquitinating activity of UCHL5 and USP14.
4. The method of claim 2, wherein the determination of the inhibition of UCHL5 and USP14 activities is conducted with an assay performed with human 19S RP and ubiquitin-AMC or HA-ubiquitin vinyl sulfone as a substrate for measuring deubiquitinating activity of UCHL5 and USP14.
5. The method of claim 1, wherein the determination of the inhibition of the one or more non-proteasomal associated DUB enzymes activities is conducted with an assay performed with human 19S RP and ubiquitin-AMC or HA-ubiquitin vinyl sulfone as a substrate for measuring deubiquitinating activity of the one or more non-proteasomal associated DUB enzymes.
6. The method of claim 2, wherein the determination of the inhibition of the one or more non-proteasomal associated DUB enzymes activities is conducted with an assay performed with human 19S RP and ubiquitin-AMC or HA-ubiquitin vinyl sulfone as a substrate for measuring deubiquitinating activity of the one or more non-proteasomal associated DUB enzymes.
7. The method of claim 3, wherein the determination of the inhibition of the one or more non-proteasomal associated DUB enzymes activities is conducted with an assay performed with human 19S RP and ubiquitin-AMC or HA- ubiquitin vinyl sulfone as a substrate for measuring deubiquitinating activity of the one or more non-proteasomal associated DUB enzymes.

8. The method of claim 4, wherein the determination of the inhibition of the one or more non-proteasomal associated DUB enzymes activities is conducted with an assay performed with human 19S RP and ubiquitin-AMC or HA-ubiquitin vinyl sulfone as a substrate for measuring deubiquitinating activity of the one or more non-proteasomal associated DUB enzymes.

* * * * *

UNITED STATES PATENT AND TRADEMARK OFFICE
CERTIFICATE OF CORRECTION

PATENT NO.      : 9,856,511 B2
APPLICATION NO. : 14/344968
DATED           : January 2, 2018
INVENTOR(S)     : Slavica Brnjic et al.

Page 1 of 1

It is certified that error appears in the above-identified patent and that said Letters Patent is hereby corrected as shown below:

On the Title Page

Item (54) and in the Specification, Line 1 change "PROTEASE" to --PROTEASOME--.

In the Claims

Claim 1, Column 18, Line 16 change "USF14" to --USP14--.

Claim 1, Column 18, Line 18 change "USF14" to --USP14--.

Signed and Sealed this
Third Day of April, 2018

Andrei Iancu
*Director of the United States Patent and Trademark Office*